(12) United States Patent
Albisser et al.

(10) Patent No.: US 8,756,043 B2
(45) Date of Patent: Jun. 17, 2014

(54) BLOOD GLUCOSE METER AND COMPUTER-IMPLEMENTED METHOD FOR IMPROVING GLUCOSE MANAGEMENT THROUGH MODELING OF CIRCADIAN PROFILES

(75) Inventors: Anthony Michael Albisser, The Villages, FL (US); Lucienne Marie Ide, Coral Gables, FL (US)

(73) Assignee: Rimidi Diabetes, Inc., Atlanta, GA (US)

( * ) Notice: Subject to any disclaimer, the term of this patent is extended or adjusted under 35 U.S.C. 154(b) by 37 days.

(21) Appl. No.: 13/559,552

(22) Filed: Jul. 26, 2012

(65) Prior Publication Data

US 2014/0032195 A1    Jan. 30, 2014

(51) Int. Cl.
| | | |
|---|---|---|
| G06G 7/48 | (2006.01) | |
| G06G 7/58 | (2006.01) | |
| G06F 13/10 | (2006.01) | |
| G01N 33/48 | (2006.01) | |
| G01N 31/00 | (2006.01) | |

(52) U.S. Cl.
USPC .......... 703/11; 703/12; 703/21; 703/22; 702/19; 702/22

(58) Field of Classification Search
None
See application file for complete search history.

(56) References Cited

U.S. PATENT DOCUMENTS

| | | | |
|---|---|---|---|
| 5,822,715 A | 10/1998 | Worthington et al. | |
| 6,024,699 A | 2/2000 | Surwit et al. | |
| 6,168,563 B1 | 1/2001 | Brown | |
| 6,421,633 B1 | 7/2002 | Heinonen et al. | |
| 6,544,212 B2 | 4/2003 | Galley et al. | |
| 6,925,393 B1 | 8/2005 | Kalaz et al. | |
| 7,025,425 B2 | 4/2006 | Kovatchev et al. | |
| 7,137,951 B2 | 11/2006 | Pilarski | |
| 7,167,818 B2 | 1/2007 | Brown | |
| 7,282,029 B1 | 10/2007 | Poulsen et al. | |

(Continued)

FOREIGN PATENT DOCUMENTS

| | | |
|---|---|---|
| EP | 834825 | 4/1998 |
| EP | 881495 | 12/1998 |

(Continued)

OTHER PUBLICATIONS

Tudor et al. (Computer Methods and Programs in Biomedicine, 1998, 56, 175-192).*

(Continued)

*Primary Examiner* — Larry D Riggs, II
(74) *Attorney, Agent, or Firm* — Patrick J. S. Inouye; Makiko Coffland

(57) ABSTRACT

A blood glucose meter and computer-implemented method for improving glucose management through modeling of circadian profiles is provided. For each daily meal period, two sets of pre- and post-meal period data are collected into a circadian profile and stored on a glucose meter, including a level of blood glucose of a diabetic patient and a dosage of diabetes medication. A model of predicted blood glucose for the patient is created from the blood glucose levels in each record as expected blood glucose values and predicted errors and visualized in a log-normal distribution. Target ranges for blood glucose at each meal period are determined and superimposed over the expected blood glucose values. Pharmacodynamics of the medication are obtained. An incremental change in dosing of the medication is propagated over a model day and the expected blood glucose values and their predicted errors are adjusted in response to the incremental dosing change.

21 Claims, 9 Drawing Sheets

(56) References Cited

U.S. PATENT DOCUMENTS

| | | |
|---|---|---|
| 7,311,666 B2 | 12/2007 | Stupp et al. |
| 7,353,152 B2 | 4/2008 | Brazhnik et al. |
| 7,356,423 B2 | 4/2008 | Nehrig |
| 7,404,796 B2 | 7/2008 | Ginsberg |
| 7,651,845 B2 | 1/2010 | Doyle et al. |
| 7,824,333 B2 | 11/2010 | Otto et al. |
| 2001/0011224 A1 | 8/2001 | Brown |
| 2001/0047252 A1 | 11/2001 | Brown |
| 2002/0022773 A1 | 2/2002 | Drinan et al. |
| 2003/0208113 A1 | 11/2003 | Mault et al. |
| 2005/0071141 A1 | 3/2005 | Butler |
| 2005/0121322 A1 | 6/2005 | Say et al. |
| 2005/0125158 A1 | 6/2005 | Schlessinger et al. |
| 2005/0234311 A1 | 10/2005 | Kouchi et al. |
| 2005/0244910 A1 | 11/2005 | Wolever et al. |
| 2006/0167345 A1 | 7/2006 | Vespasiani |
| 2006/0276771 A1 | 12/2006 | Galley et al. |
| 2007/0149861 A1 | 6/2007 | Crothall et al. |
| 2007/0282177 A1 | 12/2007 | Pilz |
| 2008/0154513 A1 | 6/2008 | Kovaltchev et al. |
| 2008/0234992 A1 | 9/2008 | Ray et al. |
| 2008/0306353 A1 | 12/2008 | Douglas et al. |
| 2009/0006061 A1 | 1/2009 | Thukral et al. |
| 2009/0036753 A1 | 2/2009 | King |
| 2009/0036828 A1 | 2/2009 | Hansen et al. |
| 2009/0164239 A1 | 6/2009 | Hayter et al. |
| 2010/0145174 A1 | 6/2010 | Alferness |
| 2010/0174553 A1 | 7/2010 | Kaufman et al. |
| 2010/0262434 A1 | 10/2010 | Shaya |
| 2011/0196213 A1 | 8/2011 | Thukral et al. |
| 2012/0046966 A1 | 2/2012 | Chang et al. |
| 2012/0172694 A1 | 7/2012 | Desborough et al. |

FOREIGN PATENT DOCUMENTS

| | | |
|---|---|---|
| EP | 1281351 | 2/2003 |
| EP | 2023256 | 2/2009 |
| WO | 01/72208 | 10/2001 |
| WO | 2004/015539 | 2/2004 |
| WO | 2007065285 | 6/2007 |

OTHER PUBLICATIONS

Rodbard, (Journal of Diabetes Science and Technology, 2009, 3(6), 1395-1401).*

K. W. Beach, "A Theoretical Model to Predict the Behavior of Glycosylated Hemoglobin Levels," Journal of Theoretical Biology, Academic Press Inc, London, pp. 547-561 (Jan. 1, 1979).

H. E. Levobitz, "Insulin Resistance: Definition and Consequences," Exp Clin Endocrinol Diabetes 109, Suppl. 2, pp. S135-S148 (2001).

Park et al., "PDA Based Point of Care Personal Diabetes Management Systems," Proceedings of the 2005 IEEE Engineering in Medicine and Biology 27th Annual Conference, Shanghai, China, Sep. 1-4, 2005, pp. 3749-3752 (Sep. 2005).

D. Mendosa, "On-Line Diabetes Resources, Part 13: Diabetes Management Software," NPL_online_diabetes_resources.pdf, retrieved from internet: < URL: http://mendosa.com/software/htm>(1995).

Mathworks, "Chapter 3. Interpolation," Feb. 15, 2008 pp. 1-27, retrieved from Internet: <URL: http://www.mathworks.com/moler/interp.pdf>.

Jacobs et al, "Nutrients, foods, and dietary patterns as exposure in research: a framework for food synergy", American Society for Clinical Nutrition, No. 78 (suppl), pp. 508S-513S (2003).

Wolever et al., "Prediction of Glucose and Insulin Responses of Normal Subjects after Consuming Mixed Meals Varying in Energy, Protein, Fat, Carbohydrate and Glycemic Index," The Journal of Nutrition, No. 126, pp. 2807-2812 (1996).

Powell et al., "International Table of Glycemic Index and Glycemic Load Values: 2002," American Society for Clinical Nutrition, No. 76, pp. 5-56 (2002).

Lehmann et al., "An Integrated Approach for the Computer-Assisted Treatment of Diabetes Patients on Insulin," Medical Informatica, Taylor and Francis, Basingstoke, GB, vol. 17, No. 2, Apr. 1, 1992, pp. 105-123.

Salzsieder et al., "A Model-Based System for the Individual Prediction of Metabolic Responses to Improve the Therapy in Type I Diabetes," Hormone and Metabolic Research, Thieme-Stratton, Stuttgart, DE, vol. 24, No. Suppl., Jan. 1, 1990, pp. 10-19 (Jan. 1, 1990).

G. Trevino, "On the Weighted-Average Relationship between Plasma Glucose and HbA1c," Diabetes Care, vol. 29, No. 29, p. 466 (Feb. 2006).

Cely et al., "Relationship of Baseline Glucose Homeostasis to Hyperglycemia during Medical Critical Illness," Chest, No. 126(3), pp. 879-887 (Sep. 2004).

R. Landgraf, "The Relationship of Postprandial Glucose to HbA1c," Diabetes/Metabolism Research and Reviews, No. 20(Suppl 2), pp. S9-S12 (2004).

Chandalia et al., "Glycated Hemoglobin," Current Science, vol. 83, No. 12, pp. 1522-1532 (Dec. 2002).

Nathan et al., "Relationship between Glycated Haemoglobin Levels and Mean Glucose Levels over Time," Diabetologia, No. 50, pp. 2239-2244 (2007).

Rohlfing et al., "Defining the Relationship between Plasma Glucose and HbA1c," Diabetes Care, vol. 25, No. 2, pp. 275-278 (Feb. 2002).

Mathworld—A Wolfram Web Resources, "Exponential_Decay", p. 1 retrieved from http://mathworld.wolfram.com/ExponentialDecay.html (last updated Aug. 7, 2012).

Tahara et al., "Kinetics of HbA1c, Glycated Albumin, and Fructosamine and Analysis of Their Weight Functions Against Preceding Plasma Glucose Level," Diabetes Care, vol. 18, No. 4, pp. 440-447 (Apr. 1995).

Tahara et al., "The Response of GHb to Stepwise Plasma Glucose Change Over Time in Diabetic Patients," Diabetes Care, vol. 16, No. 9, pp. 1313-1314 (Sep. 1993).

Nuttall et al., "Metabolic Response of People with Type 2 Diabetes to a High Protein Diet," Nutrition & Metabolism, No. 1:6, pp. 1-7 (2004).

Ramlo-Halsted et al., "The Natural History of Type 2 Diabetes: Practical Points to Consider in Developing Prevention and Treatment Strategies," Clinical Diabetes, vol. 18, No. 2, pp. 1-10 (2000).

Simpson et al., "Macronutrients Have Different Metabolic Effects in Nondiabetics and Diabetics," The American Journal of Clinical Nutrition, No. 42, pp. 449-453 (Sep. 1985).

Gannon et al., "Oral Arginine Does Not Stimulate an Increase in Insulin Concentration but Delays Glucose Disposal," The American Journal of Clinical Nutrition, No. 76, pp. 1016-1022 (2002).

Mander et al., "Co-Ingestion of a Protein Hydrolysate and Amino Acid Mixture with Carbohydrate Improves Plasma Glucose Disposal in Patients with Type 2 Diabetes," The American Journal of Clinical Nutrition, No. 82, pp. 76-83 (2005).

Van Loon et al., "Amino Acid Ingestion Strongly Enhances Insulin Secretion in Patients with Long-Term Type 2 Diabetes," Diabetes Care, vol. 26, No. 3, pp. 625-630 (Mar. 2003).

Golkar, S. M. et al., "Assessment of the relationship between glucose and A1c using kinetic modeling", Journal of Diabetes and Its Complications 20 (2006) 285-294.

Kovatchev, B. P. et al., "Algorithmic Evaluation of Metabolic Control and Risk of Severe Hypoglycemia in Type 1 and Type 2 Diabetes Using Self-Monitoring Blood Glucose Data", diabetes Technology and Therapeutics, vol. 5, No. 5, 2003, p. 817-828.

Svendsen, P. A. et al., "Glycosylated Haemoglobin and Steady-State Mean Blood Glucose Concentration in Type 1 (insulin-Dependent) Diabetes", Diabetologia (1982) 23:403-405.

Chan et al., "Pharmacological Management of Type 2 Diabetes Mellitus: Rationale for Rational Use of Insulin," Mayo Clinic Proc., No. 78, pp. 459-467 (2003).

Shafiqul et al., "Peak Blood Glucose Prediction Algorithm Following a Meal Intake," IEEE Canadian Conference on Electrical and Computer Engineering, pp. 579-582 (Jul. 30, 2007).

Tresp et al., "Neural Network Models for the Blood Glucose Metabolism of a Diabetic," IEEE Transactions of Neural Networks, pp. 1-24 (1999).

(56) References Cited

OTHER PUBLICATIONS

Reed, K. et al. "Interactive Educational Diabetes/Insulin Tutorial at www.2aida.info", Diabetes Technology & Therapeutics, vol. 8, No. 1, p. 126-137 (2006).
Bergman, et al., "Quantitative Estimation of Insulin Sensitivity," The American Physiological Society, No. 236(6), p. E667-E677 (1979).
"Insulin Activity Curves," pp. 1-2, retrieved from http://members.tripod.com/diabetics_world/Human_Animal_Activity.htm#Human (last visited Aug. 10, 2012).
Eli Lilly Co., Ltd., "Insulin Humaject Information" retrieved from http://www.drugs.com/uk/humaject-pens-prefilled-insulin-pens-soluble-mixture-3-spc-3458.html (last visited Aug. 2011).
"Chapter Two Rate of Change: The Derivative," pp. 1-44, retrieved from http://media.wiley.com/product_data/excerpt/63/EHEP0005/EHEP000563-2.pdf (last visited Aug. 10, 2012).
Lilly USA, LLC., "Highlights of Prescribing Information," May 18, 2011 pp. 1-12.
Stickle D. et al. "A kinetic mass balance model for 1, 5-anhydroglucitol: applications to monitoring of glycemic control", Endocrynology and Metabolism, vol. 273, No. 4, p. E821, Jan. 1, 1997.
McGill J. B. et al. "Circulating 1, 5-anhydroglucitol levels in adult patients with diabetes reflect longitudinal changes of glycemia: a U.S. trial of the GlycoMark assay", Diabetes Care, american Diabetes Association, alexandria, VA, US, vol. 27, No. 8, p. 1859-1865, Aug. 1, 2004.
Nowatzke W. et al. "Evaluation of an assay for serum 1, 5-anhydroglucitol(GlycoMark™) and determination of reference intervals on the Hitachi 917 analyzer", Clinical Chimica ACTA, Elsevier BV, Amsterdam, NL, vol. 350, No. 1-2, p. 201-209, Dec. 1, 2004.
Albisser et al., "Home Blood Glucose Prediction: Validation, Safety, and Efficacy Testing in Clinical Diabetes," Diabetes Technology Therapeutics, Jun. 2005, vol. 7, No. 3, pp. 487-496.
Albisser et al., "Home Blood Glucose Prediction: Clinical Feasibility and Validation in Islet Cell Transplantation Candidates," Diabetologia, Jul. 2005, vol. 48, No. 7, pp. 1273-1279.
Rohlfing et al., "Defining the Relationship Between Plasma Glucose and HbA(1c): Analysis of Glucose Profiles and HbA(1c) in the Diabetes Control and Complications Trial," Diabetes Care, Feb. 2002, vol. 25, No. 2, pp. 275-278.
Albisser and Inhaber, "Automation of the Consensus Guidelines in Diabetes Care: Potential Impact on Clinical Inertia," Endocrine Practice, Nov.-Dec. 2010, vol. 16, No. 6, pp. 992-1002.
Albisser et al., "Closing the Circle of Care with New Firmware for Diabetes: MyDiaBase+RxChecker," J Diabetes Sci Technol., May 2009, vol. 3, No. 3, pp. 619-623.
Albisser et al., "Prescription Checking Device Promises to Resolve Intractable Hypoglycemia," J Diabetes Sci Technol., May 2009, vol. 3, No. 3, pp. 524-532.
Albisser, "Technophobia, Prescription Checking and the Future of Diabetes Management," Diabetologia, Jun. 2009, vol. 52, No. 6, pp. 1013-1018.
Choleau et al., "A Novel Method for Assessing Insulin Dose Adjustments by Patients with Diabetes," J Diabetes Sci Technol., Jan. 2007, vol. 1, No. 1, pp. 3-7.
Albisser et al., "Averting Iatrogenic Hypoglycemia Through Glucose Prediction in Clinical Practice: Progress towards a New Procedure in Diabetes," Diabetes Res Clin Pract., May 2007, vol. 76, No. 2, pp. 207-214.
Albisser et al., "How Good is Your Glucose Control?" Diabetes Technol Ther., Dec. 2005, vol. 7, No. 6, pp. 863-875.
Albisser, "A Graphical User Interface for Diabetes Management That Integrates Glucose Prediction and Decision Support," Diabetes Technol Ther., Apr. 2005, vol. 7, No. 2, pp. 264-273.
Albisser et al., "Patient Confidentiality, Data Security, and Provider Liabilities in Diabetes Management," Diabetes Technol Ther., 2003, vol. 5, No. 4, pp. 631-640.
Albisser, "Analysis: Toward Algorithms in Diabetes Self-Management," Diabetes Technol Ther., 2003, vol. 5, No. 3, pp. 371-373.
Albisser A.M. et al., "The Impact of Initiatives in Education, Self-Management Training, and Computer-Assisted Self-Care on Outcomes in Diabetes Disease Management," Diabetes Technol Ther., 2001 Winter, vol. 3, No. 4, pp. 571-579.
Albisser et al., "Information Technology and Home Glucose Clamping," Diabetes Technol Ther., 2001 Fall, vol. 3, No. 3, pp. 377-386.
Albisser, "Clinical Studies with Home Glucose Clamping," Ann Endocrinol (Paris), Feb. 2001, vol. 62 No. 1, Pt 1, pp. 11-18.
Albisser et al., "Getting Referrals for Diabetes Education and Self-Management Training," Diabetes Educ., Nov.-Dec. 1999, vol. 25 No. 6, pp. 959-960, 963-964, 966 passim.
Meneghini, et al., "An Electronic Case Manager for Diabetes Control," Diabetes Care., Apr. 1998, vol. 21, No. 4, pp. 591-596.
Naylor et al., "Comparison of Parametrized Models for Computer-Based Estimation of Diabetic Patient Glucose Response," Med Inform (Lond), Jan.-Mar. 1997, vol. 22, No. 1, pp. 21-34.
Albisser et al., "Diabetes Intervention in the Information Age," Med Inform (Lond), Oct.-Dec. 1996, vol. 21, No. 4, pp. 297-316. Erratum in: Med Int (Lond), Apr.-Jun. 1997, vol. 22, No. 2, p. 205.
Angelico et al., "Use of an On-Line Computer System for Quantifying Insulin Requirements Before and After Islet Cell Transplantation: First Experience," Transplant Proc., Dec. 1995, vol. 27, No. 6, p. 3173.
Rodbard et al., "American Association of Clinical Endocrinologists Medical Guidelines for Clinical Practice for the Management of Diabetes Mellitus," Endocr Pract., May-Jun. 2007, vol. 13, Suppl. 1, pp. 1-68.
Rodbard et al., "Statement by an American Association of Clinical Endocrinologists/American College of Endocrinology Consensus Panel on Type 2 Diabetes Mellitus: an Algorithm for Glycemic Control," Endocr Pract., 2009, vol. 15, No. 6, pp. 540-559.
Funnell et al., "National Standards for Diabetes Self-Management Education," Diabetes Educ. 2007, vol. 33, No. 4, pp. 599-614.
Lachin et al., "Effect of Glycemic Exposure on the Risk of Microvascular Complications in the Diabetes Control and Complications Trial—Revisited," Diabetes. Apr. 2008, vol. 57, No. 4, pp. 995-1001.
Nathan, "Finding new treatments for diabetes—how Many, How Fast, . . . How Good?" N Engl J Med, Feb. 2007, vol. 356, No. 5, pp. 437-440.
Diabetes Control and Complications Trial Research Group, "The Effect of Intensive Treatment of Diabetes on the Development and Progression of Long-Term Complications in Insulin-Dependent Diabetes Mellitus," N Engl J Med, Sep. 1993, vol. 329, No. 14, pp. 977-986.
Hirsch et al., "A Real-World Approach to Insulin Therapy in Primary Care Practice," Clinical Diabetes, 2005, vol. 23, No. 2, pp. 78-86.
UK Prospective Diabetes Study Group, "Intensive Blood-Glucose Control with Sulphonylureas or Insulin Compared with Conventional Treatment and Risk of Complications in Patients with Type 2 Diabetes (UKPDS 33)," Lancet, Sep. 1998, vol. 352, Issue 9131, pp. 837-853.
The DCCT Research Group, "Epidemiology of severe hypoglycemia in the Diabetes Control and Complications Trial," Am J Med., Apr. 1991, vol. 90, pp. 450-459.
Cryer, "Hypoglycemia: Still the Limiting Factor in the Glycemic Management of Diabetes," Endocr Pract., Sep. 2008, vol. 14, No. 6, pp. 750-756.
Laprie (Ed), "Dependability: Basic Concepts and Terminology," Springer-Verlag, Wein, New York, 1992.
Drab, "Translating Clinical Guidelines into Clinical Practice: Role of the Pharmacist in Type 2 Diabetes Management," J Am Pharm Assoc., Nov.-Dec. 2009, vol. 49, No. 6, pp. 152-162.
Kirwin et al., "Pharmacist Recommendations to Improve the Quality of Diabetes Care: A Randomized Controlled Trial," Journal of Managed Care Pharmacy, Mar. 2010, vol. 16, No. 2, pp. 104-113.
Armor et al., "A Review of Pharmacist Contributions to Diabetes Care in the United States," Journal of Pharmacy Practice, 2010, vol. 23, No. 3, pp. 250-264.
Campbel, "Role of the Pharmacist in Diabetes Management," Am J Health-Syst Pharm, Dec. 2002, vol. 59, Suppl. 9, pp. S18-S21.
Palaian et al., "Role of Pharmacist in Counseling Diabetes Patients," The Internet Journal of Pharmacology, 2005, vol. 4, No. 1.

(56) References Cited

OTHER PUBLICATIONS

Worthington, "Controlling Boold Glucose: Insights from an Engineering Control Systems Perspective," Med Inform, 1997, vol. 22, No. 1, pp. 5-19.

Canadian Pharmacists Association, "The Diabetes Strategy for Pharmacists," http://diabetespharmacists.ca/ (last visited Aug. 10, 2012).

Life Scan, Inc., "One Touch Verio IQ Blood Glucose Monitoring System Owner's Booklet: Instructions for Use," Mar. 2011.

Dungan, "1,5 Anhydroglucitol and Postpandrial Hyperglycemia as Measured by Continuous Glucose Monitoring System in Moderately Controlled Patients With Diabetes", Diabetes Care, vol. 29, No. 6, Jun. 2006, 1214-1219.

Kilpatrick et al:"Plasma 1,5 anhydroglucitol concentrations are influenced by variations in the renal threshold for glucose", 1999, Diabetic Medicine, 16, 496-499.

Akanuma et al. "Urinary excretion of 1,5-anhydro-D-glucitolaccompanying glucose excretion in diabetic patients", Diabetologia (1988)31 : 831 835.

Pitkanen, "Mannose, mannitol, fructose and 1,5-anhydroglucitol concentrations measured by gas chromatography/mass spectrometry in blood plasma of diabetic patients", Clinica Chimica Acta 251 (1996) 91-103.

Suzuki et al:"Production of 1,5-anhydroglucitol from 1,5-anhydrofructose in arythroleukemia cells", Eur. J. Biochem. 240, 23-29 (1996).

Yamanouchi et al. "Origin and disposal of 1,5 anhydroglucitol, a major polyol in the human body", Am. J. Physiol. 263 (Endocrinol. Metab. 26): E268-E273, 1992.

Yamanouchi et al. "Reduction of plasma 1,5-anhydroglucitol (1-deoxyglucose) concentration in diabetic patients" Diabetologia, vol. 31, No. 1,1988, p. 41-45.

Yamanouchi et al. "1,5-Anhydroglucitol stimulates insulin relase in insulinoma cell lines", Biochimica et Biophysica Acta 1623 (2003) 82-87.

Frohnauer et al. "Graphical Human-Insulin time-Activity Profiles Using Standardized Definitions" Diebetes Technology and Therapeutics; vol. 3, No. 3, 2001, p. 419-429.

Perez-Martin et al. Simplified Measurement of Insulin Sensitivity with the Minimal Model Procedure in Type 2 diabetic patients without measurements of insulinemia, Horm Metab Research, 2002; 34:102-106.

O'Leary et al., "Exercise-Induced reversal of Insulin Resistance in Obese Elderly Is Associated With Reduced Visceral Fat," J Appl Physiol 100: 1584-1589, 2006.

Ramgovind et al., "The Management of Security in Cloud Computing". IEEE, Information Security for South Africa, (ISSA), Aug. 2-4, 2010, 1-7.

Deutsch T. et al., "The principles and prototyping of a knowledge-based diabetes management system", Computer methods and programs in biomedicine, Elsevier, Amsterdam, NL vol. 29, No. 2, Jun. 1, 1989, pp. 75-88.

\* cited by examiner

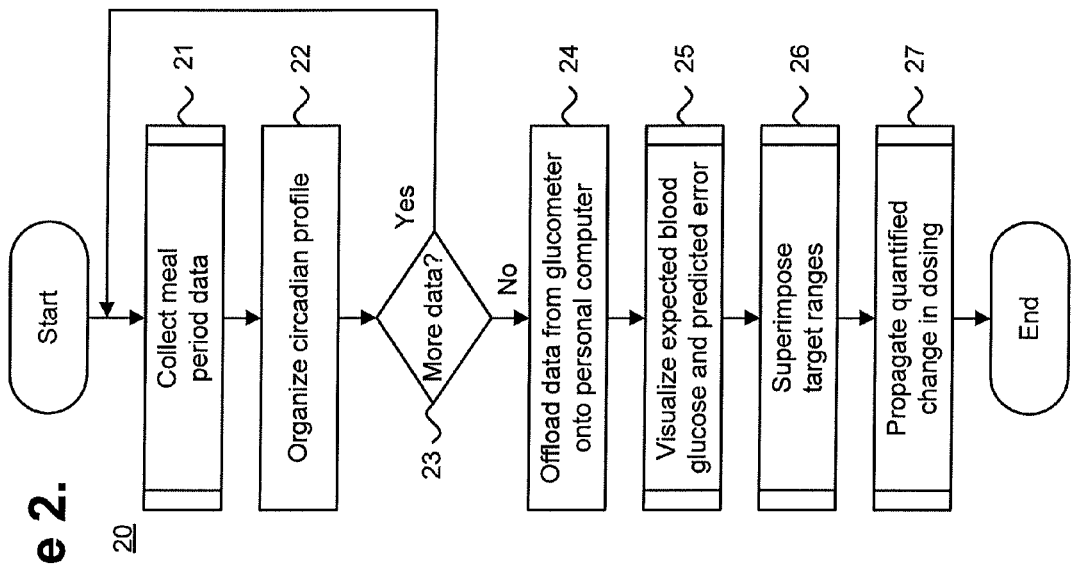
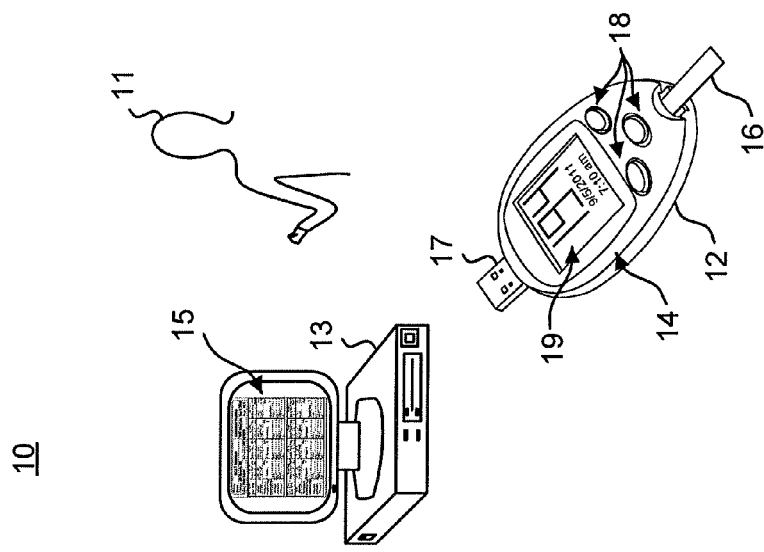

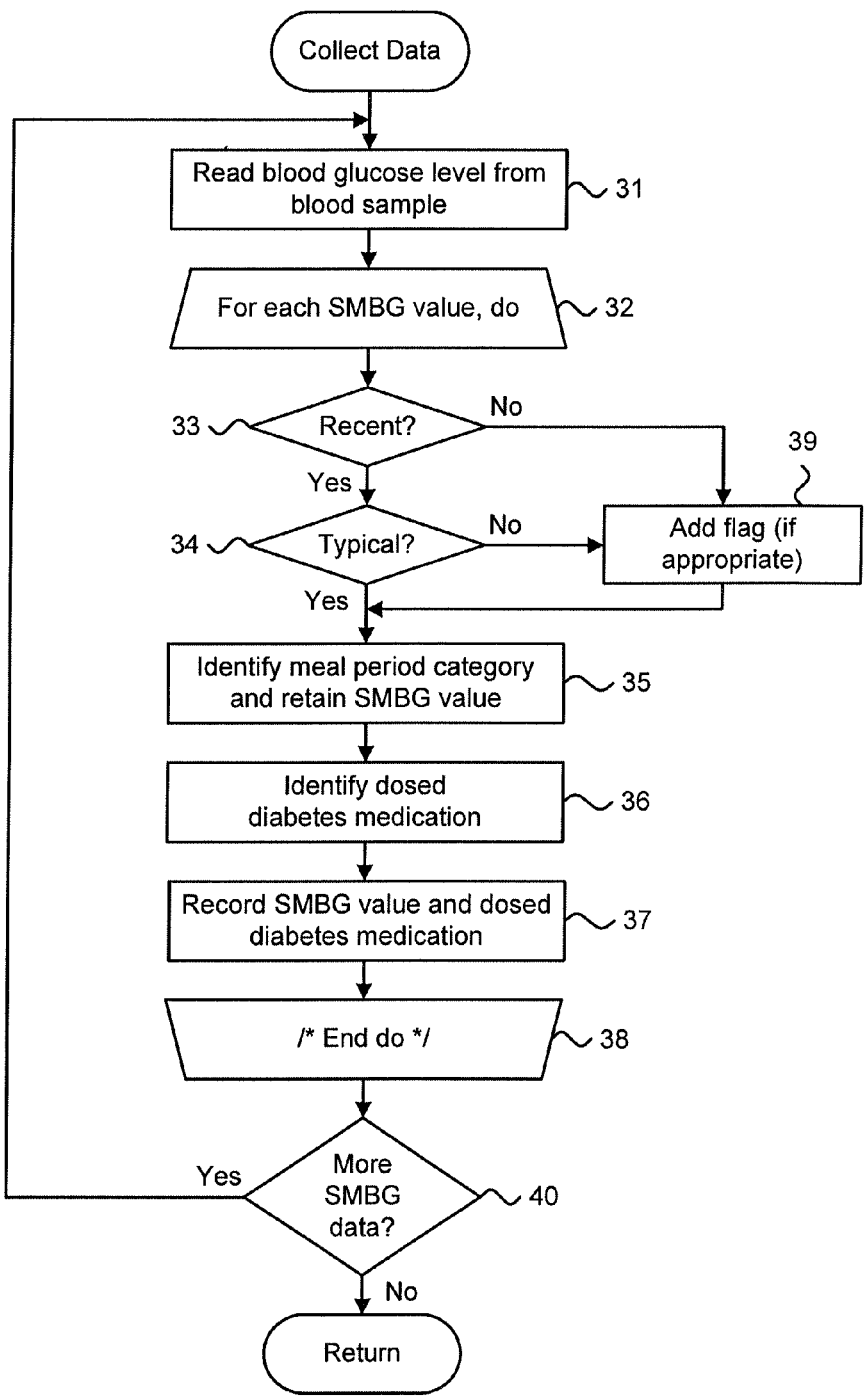

Figure 4.

| Medical Center: | Central Hospital | | | | | | | | | | | Circadian Profiles | |
|---|---|---|---|---|---|---|---|---|---|---|---|---|---|
| Physician: | R. Kimble, MD | | | | | | | | | | | MPP Start Date: Sep 5, 2011 | |
| Patient: | Dan Cooper | | Hx Number: 487 52 9733 | | | | | | | | | Height: 74 | |

| MP Profiles | Breakfast | | | Lunch | | | Dinner | | | Bedtime | | |
|---|---|---|---|---|---|---|---|---|---|---|---|---|
| BW1: 209 | Before B | After B | Mid B-L | Before L | After L | Mid L-D | Before D | After D | Mid D-S | Before S | After S | Over Night |
| SMBG (hh:mm) | 194 7:10 | 63 8:40 | | 144 13:50 | 163 15:20 | | 141 17:20 | 48 18:50 | | 123 22:00 | | 124 3:30 |
| Medications Shorter-acting Longer-acting | 6 Apidra | | Site T | 4 Apidra | | Site T | 6 Apidra | | Site T | 18 Lantus | | Site T |
| Life-style comments (Optional) | CHO | | | CHO | | | CHO | | | CHO | | |
| | EX | | | EX | | | EX | | | EX | | |
| | Stress | | | Stress | | | Stress | | | Stress | | |
| | etc | | | etc | | | etc | | | etc | | |

| MP Profiles | Breakfast | | | Lunch | | | Dinner | | | Bedtime | | |
|---|---|---|---|---|---|---|---|---|---|---|---|---|
| BW2: 206 | Before B | After B | Mid B-L | Before L | After L | Mid L-D | Before D | After D | Mid D-S | Before S | After S | Over Night |
| SMBG (hh:mm) | 167 8:50 | 99 10:20 | | 99 14:00 | 211 15:30 | | 122 18:30 | 60 20:00 | | 120 21:50 | | 180 2:50 |
| Medications Shorter-acting Longer-acting | 6 Apidra | | Site T | 4 Apidra | | Site T | 6 Apidra | | Site T | 18 Lantus | | Site T |
| Life-style comments (Optional) | CHO | | | CHO | | | CHO | | | CHO | | |
| | EX | | | EX | | | EX | | | EX | | |
| | Stress | | | Stress | | | Stress | | | Stress | | |
| | etc | | | etc | | | etc | | | etc | | |

Figure 11.

Circadian Profiles — 130

| Medical Center: | Central Hospital | | | | | | | | | | | |
|---|---|---|---|---|---|---|---|---|---|---|---|---|
| Physician: | R. Kimble, MD | | | | | MPP Start Date: Sep 5, 2011 | | | | | | |
| Patient: | Dan Cooper | | | Hx Number: 487 52 9733 | | | | | Height: 74 | | | |

| MP Profiles | Breakfast | | | Lunch | | | Dinner | | | Bedtime | | |
|---|---|---|---|---|---|---|---|---|---|---|---|---|
| BW1: 209 | Before B | After B | Mid B-L | Before L | After L | Mid L-D | Before D | After D | Mid D-S | Before S | After S | Over Night |
| SMBG (hh:mm) | 100 7:15 | 120 8:30 | | 100 12:30 | 120 13:15 | | 100 17:00 | 120 18:00 | | 100 22:00 | | 130 3:30 |
| Medications Shorter-acting | 6 Apidra | Site T | | 4 Apidra | Site ◆ T | | 6 Apidra | Site T | | | | Site T |
| Longer-acting | | | | | | | | | | 18 Lantus | | |
| Life-style comments (Optional) | Usual after lunch activity increased with mild exercise at level 1. | | | | | | | | | | | |

— 131, 132

| MP Profiles | Breakfast | | | Lunch | | | Dinner | | | Bedtime | | |
|---|---|---|---|---|---|---|---|---|---|---|---|---|
| BW2: 206 | Before B | After B | Mid B-L | Before L | After L | Mid L-D | Before D | After D | Mid D-S | Before S | After S | Over Night |
| SMBG (hh:mm) | 167 8:50 | 99 10:20 | | 99 14:00 | 211 15:30 | | 122 18:30 | 60 20:00 | | 120 21:50 | | 180 2:50 |
| Medications Shorter-acting | 6 Apidra | Site T | | 4 Apidra | Site T | | 6 Apidra | Site T | | | | Site T |
| Longer-acting | | | | | | | | | | 18 Lantus | | |
| Life-style comments (Optional) | CHO | | | CHO | | | CHO | | | CHO | | |
| | EX | | | EX | | | EX | | | EX | | |
| | Stress | | | Stress | | | Stress | | | Stress | | |
| | etc | | | etc | | | etc | | | etc | | |

BLOOD GLUCOSE METER AND COMPUTER-IMPLEMENTED METHOD FOR IMPROVING GLUCOSE MANAGEMENT THROUGH MODELING OF CIRCADIAN PROFILES

FIELD

The present invention relates in general to glycemic management in diabetic patients and, in particular, to a blood glucose meter and computer-implemented method for improving glucose management through modeling of circadian profiles.

BACKGROUND

As a chronic and incurable disease, diabetes mellitus requires continuing care that lasts throughout the life of the patient. Both caregivers and patients alike are expected to play an active role in managing diabetes, regardless of form, whether Type 1, Type 2, gestational, or other. Diabetes patients are typically coached by their caregivers on lifestyle modification and educated to understand the affects of diet, especially carbohydrates, body weight, physical activity, medications, and stress on their diabetic condition. Diabetes patients are also trained and encouraged to regularly test their blood glucose levels with the assistance of a portable glucose meter ("glucometer"). In addition, medication-treated patients learn to undertake daily self-administration of medications and, where appropriate, determine corrective medication dosing to counteract postprandial glycemic rise. All diabetes patients are expected to document their self-care in a daily diary that typically chronicles their daily self-monitored blood glucose values, medications, physical activity, and dietary intake.

In turn, caregivers follow their diabetes patients on a periodic basis and work to ensure their compliance with the consensus guidelines and mandatory targets (CG&MT), which have been formulated and are regularly updated by the American Association of Clinical Endocrinologists (AACE) and the American College of Endocrinology (ACE), as well as the American Diabetes Association (ADA). At each patient consultation, a caregiver may evaluate the patient's daily diary to identify patterns in the pre-meal data, which can include examining particular examples of the patient's actions to determine underlying causes for any outcomes suffered, above all, episodes of hypoglycemia. Additionally, the caregiver will normally test the patient's level of glycated hemoglobin ("A1c") to establish accord with the current CG&MT target for well-managed diabetes. As needed, the caregiver may adjust the patient's oral anti-diabetic medications or insulin dosing to hopefully move the patient's blood glucose and A1c levels closer to the mandated targets.

The roles respectively performed by caregivers and their diabetic patients form a "circle of care" that requires each patient to provide their own data and do those actions necessary that together allow the caregivers to effectively manage the patient's diabetic condition. At a minimum, each patient is expected to self monitor their blood glucose levels and comply with each caregiver's instructions. Obversely, the caregivers are expected to monitor the patient's condition and provide apt guidance through changes in medications and lifestyle as needed to achieve perfect diabetes control as mandated in the various guidelines.

Notwithstanding, the circle of care generally remains incomplete. Conventional diabetes management efforts are in practice remarkably retrospective due to the significant focus on past patient condition, as seen through the patient's self-monitored blood glucose values that ordinarily extend back over several prior months. In turn, armed at best with the historical values of blood glucose testing, as sometimes confirmed by A1c results, a caregiver endeavors to control the future direction of ongoing diabetes treatment typically for the next several months until the next consultation. This control is exercised chiefly by making adjustments to medications, typically focused on insulin, with the intent of somehow moving patient blood glucose levels and A1c to target, and often without demanding data more reflective of the patient's true condition at the time of consultation.

Some types of conventional glucometers attempt to bridge the gap in the circle of care by assisting patients in their own between-consultation diabetes self-management efforts. Basic glucometers merely calculate and display blood glucose levels by reading a disposable test strip upon which the patient has placed a drop of blood. However, so-called "smart" glucometers typically include an internal memory that electronically records the results of each blood glucose test, along with the date and time of testing. The stored blood glucose data can then be made available for download to a personal computer. In addition, when available, onboard software can calculate an average of recent blood glucose levels and identify trends and patterns in the blood glucose data. Notwithstanding, the decision on whether diabetes medication dosing or other changes are appropriate remains solely at the discretion of the patient or follow-on caregiver consultation.

The incompleteness of the circle of care contributes to the dilemma faced by caregivers in managing diabetes, which suggests that satisfactory glycemic control is seemingly only achievable with unsatisfactory risk of hypoglycemia, as well as the converse. The CG&MT recommends a fasting blood glucose level of less than 110 mg/dL (non-fasting less than 140 mg/dL) and A1c between 6% and 7%, with patients generally being asked to strive for A1c of less than 7% (and less than 6.5% according to other standards). Achieving these goals, however, carries the adverse consequence of increasing the risks of treatment-related hypoglycemia, which caregivers counter by changing diet or medication dosing that then shifts that patient's blood glucose level outside the CG&MT target range. Consequently, a self-reinforcing vicious cycle is formed, as increased medication dosing to reduce glycemic values into mandated target ranges results in increased hypoglycemic risk that a patient must counteract by eating more with an ensuing gain in body weight that induces further diabetes medication dosing change.

Therefore, a need remains for providing an improved approach to glycemic control that shifts the focus of diabetes management efforts away from retrospective blood glucose histories, such as stored on a glucometer, to recent and representative glycemic indications that better tie caregiver efforts and glucose management to actual, realized and timely patient need.

SUMMARY

A portable glucometer implements a patient database that organizes the results of SMBG testing into a circadian profile. The circadian profile is offloaded and processed to accurately model expected blood glucose values and their expected error by using only the SMBG data stored in a near-term observational time frame, typically a week, immediately preceding the next caregiver consultation. Only validated (recent and typical) SMBG values are used in predicting expected glycemic outlook, thereby ensuring a reliable model. The caregiver can then explore changes to medication dosing, which can include all manner of anti-diabetes drugs, including insulin and oral agents, with confidence that the new dosing will both move the patient's glycemic control into the desired target ranges and avoid the deleterious risk of treatment-related hypoglycemia.

One embodiment provides a blood glucose meter and computer-implemented method for improving glucose management through modeling of circadian profiles. For each of a plurality of daily meal periods occurring over a recent observational time frame, at least two sets of pre- and post-meal period data are collected into a circadian profile stored on a glucose meter. A level of blood glucose on a test strip provided to the glucose meter by a diabetic patient is read for one of the daily meal periods. A dosing of diabetes medication, which was dosed during the same daily meal period as the reading of the blood glucose level, is identified. The blood glucose level and the diabetes medication dosing are stored into the circadian profile in a record for the daily meal period. Predicted blood glucose for the patient is modeled. A model comprising expected blood glucose values and their predicted errors at each daily meal period is created from the blood glucose levels in each record in the circadian profile and the model of the expected blood glucose values and their predicted errors is visualized in a preferably log-normal distribution. Target ranges for blood glucose at each meal period are determined and the target ranges are superimposed over the expected blood glucose values. Pharmacodynamics of the diabetes medication are obtained. An incremental change in dosing of the identified diabetes medication is propagated over the model day and the expected blood glucose values and their predicted errors is adjusted in response to the suggested incremental dosing change.

A further embodiment provides a blood glucose meter and computer-implemented method for managing diabetes using a glucose meter with circadian profiles. A database is structured on a glucose meter and includes a plurality of records. Each record includes a circadian profile. Each circadian profile is divided into meal period categories. Typical measurements of pre-meal and post-meal self-measured blood glucose occurring over a recent observational time frame are stored into each of the meal period categories in at least two of the circadian profiles. Diabetes medication dosed during each of the meal period categories is stored in at least two of the circadian profiles. A program is stored on the glucose meter for modeling predicted blood glucose levels on a suitably-programmed computer or mobile computing device, such as a smart phone. The self-measured blood glucose measurements are collected along a category axis, which includes each of the meal period categories. Expected blood glucose values and their predicted errors are determined from the self-measured blood glucose measurements at each meal period category on the category axis and the expected blood glucose values and their predicted errors for a model day are visualized in a log-normal distribution. A suggested incremental change in dosing of the diabetes medication over the model day is suggested and the visualized expected blood glucose values and their predicted errors are adjusted based on pharmacodynamics of the diabetes medication in proportion to the incremental change in dosing.

For certain types of diabetes patients, the approach removes the need for repeated SMBG testing throughout each day and extending over the entire course of time separating caregiver consultations. Type 2 diabetes patients, for instance, would only need to collect a minimum of two SMBG results per meal period in the week prior to consultation. Moreover, with this approach, glycemic management can be performed in an intermittent "batch" processing fashion and not in real time.

The approach also enhances caregiver confidence, as the predicted blood glucose levels and their error ranges are based on recent and typical patient data. The caregiver is then able to treat to target and safely prescribe medication dosing changes, which can include all manner of anti-diabetes drugs, including insulin and oral agents, with a high degree of confidence of attaining the results desired.

Still other embodiments of the present invention will become readily apparent to those skilled in the art from the following detailed description, wherein is described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

BRIEF DESCRIPTION OF THE DRAWINGS

FIG. 1 is a block diagram showing a blood glucose meter for improving glucose management through modeling of circadian profiles, in accordance with one embodiment.

FIG. 2 is a flow diagram showing a computer-implemented method for improving glucose management with a glucometer through modeling of circadian profiles, in accordance with one embodiment.

FIG. 3 is a flow diagram showing a routine for collecting meal period data into the circadian profile stored on the glucometer for use in the method of FIG. 2.

FIG. 4 is a user interface diagram showing, by way of example, an interactive screen for a circadian profile for use in the system of FIG. 1.

FIG. 11 is a user interface diagram showing, by way of example, an interactive screen for a circadian profile for use in a further embodiment of the system of FIG. 1.

DETAILED DESCRIPTION

Figure 6:
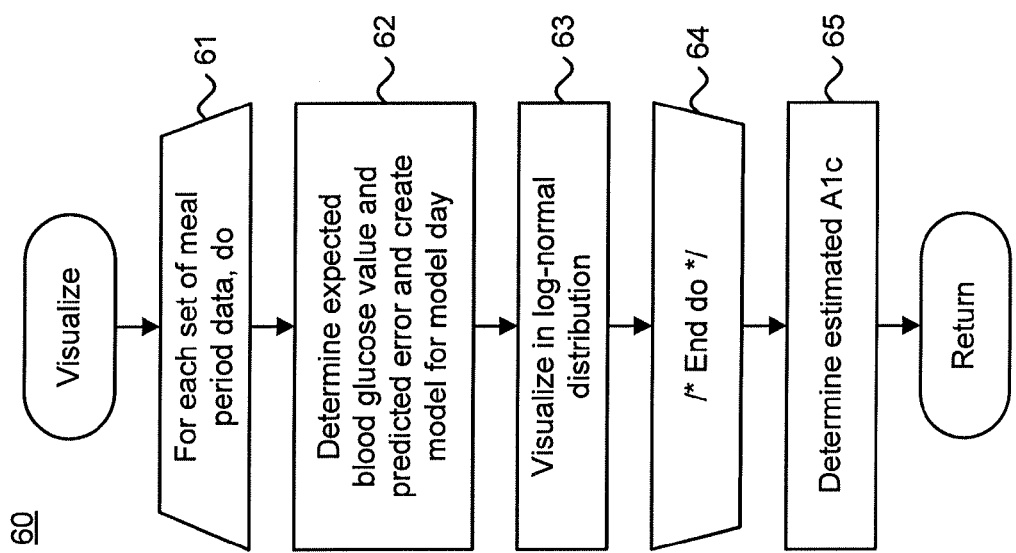
FIG. 6 is a flow diagram showing a routine for superimposing target ranges over the expected blood glucose values and predicted errors for use in the method of FIG. 2.

Ideal glycemic control in a diabetes patient occurs when the average value of self-measured blood glucose (SMBG) at each point in a circadian diabetes profile falls within a specific target range. The efficacy of current diabetes control when using a blood glucose meter ("glucometer") can be improved to help make possible ideal glycemic management by harnessing the statistical properties of blood glucose and biologic rhythmicity, when represented as categorical, not time series, data, to predict circadian profiles of expected blood glucose values. FIG. 1 is a block diagram showing a glucometer 12 for improving glucose management through modeling of circadian profiles, in accordance with one embodiment. Circadian profiles close the heretofore-incomplete circle of care and remove the danger of clinical diabetes medication prescription errors, which have been caused by overly retrospective glycemic focus and chiefly by making adjustments to medications, typically focused on insulin.

Physically, a glucometer 12 and a personal or laptop computer 13, or, alternatively, a mobile computing device, such as a smart phone, together form a diabetes management system 10, which provides guidance that helps a patient 11 improve glycemic control. The system 10 requires two principal software components to manage diabetes. First, a patient-oriented structured database 14 is implemented on a glucometer 12, which stores and organizes SMBG values, medication dosing for all types of anti-diabetes drugs, including insulin and oral agents, and related information into a circadian profile database. Second, a caregiver-centric consultation program 15 executes on a personal or laptop computer 13 or mobile computing device. The program 15 generates predictive circadian profiles for use in following diabetes patients and ensuring their CG&MT compliance, but without the dilemma of treatment-induced increased hypoglycemic risk.

The glucometer 12 is a "smart" suitably-programmed glucometer that includes an internal memory that electronically records the results of each blood glucose test, along with the date and time of testing, into the database 14. Additionally, the glucometer 12 has a visual display 19 and a set of input controls 18, such as buttons, that together form a user interface through which SMBG testing and diabetes medication dosing data, as well as other optional but useful patient information, can be entered. The glucometer 12 is capable of collecting and storing the patient's diabetes management data onboard for later offload to the personal or laptop computer 13 or mobile computing device via a built-in data interface port 17, such as a USB interface plug or other wireless or wired adapter. In a further embodiment, the glucometer 12 is provided as an external "glucophone," that is, a smart phone that has a built-in or add-on glucometer, and the database 14 and the program 15 are stored on and maintained by the glucophone.

When in use by the patient 11, the glucometer 12 calculates and displays blood glucose level by reading a disposable test strip 16 upon which the patient 11 has placed a drop of blood. With the reading of the test strip 16, the patient 11 uses the input controls 18 to validate and then identify the current category of meal period, for instance, pre-breakfast. The SMBG measurement is then stored by the glucometer 12 into the patient's circadian profile under the indicated meal period category. Optionally, the patient 11 can also enter other patient information into the glucometer 12, such as physical activity, diet and stress at each meal period, and daily body weight. The patient's data are internally stored in the database 14 on the glucometer 12, which is secured, private and password-protected, and both current and previously stored data can be accessed.

Both the database 14 and program 15 are stored on the glucometer 12. Alternatively, only the database 14 need be stored on the glucometer 12 and the program 15 can be stored and distributed separately, such as on a non-transitory computer-readable storage medium. The database 14 and program 15 could also be stored on a portable media device 12, such as a USB flash drive or other form of non-transitory removable computer-readable storage medium, such as described in commonly-assigned U.S. Patent application Publication No. 2014/0032196, pending, the disclosure of which is incorporated by reference.

To offload the database 14 and execute the program 15, the glucometer 12 is interfaced with a suitably-programmed computer, such as the personal or laptop computer 13, mobile computing device, or other compatible computing device, which then loads the necessary program, library and data files. For instance, when implemented with a USB interface plug, the glucometer 12 is inserted into a USB port on the personal or laptop computer 13 or mobile computing device. Once installed, the database 14 and program 15 are personalized, if not already personalized by using the glucometer's user interface, with the patient's and his caregiver's demographic information. The patient 11 can then optionally enter additional recent SMBG values, lifestyle, and diabetes medication details for all types of anti-diabetes drugs, including insulin and oral agents, into the database 14. His caregiver performs a similar offload and installation process on his computer and executes the program 15, which provides circadian profile-based predictions of blood glucose values and their expected errors, incremental suggestions and modeling of changes to medication dosing, and diabetes patient counseling points. Alternatively, the functionality of the program 15 could be provided through a so-called "cloud" computing infrastructure, in which patients' diabetes management data are stored online over a wide area public data network, such as the Internet, or other network infrastructure and the program 15 can be remotely executed as a Web-implemented application or smart phone "app," such as described in commonly-assigned U.S. Patent application Publication No. 2014/0032194, pending, the disclosure of which is incorporated by reference.

The database 14 and program 15 collaboratively facilitate the achievement of improving glycemic management by respectively chronicling relevant patient self-management efforts with the assistance of the glucometer 12 and predictively modeling glycemic outcomes for caregiver review and utilization. FIG. 2 is a flow diagram showing a computer-implemented method 20 for improving glucose management with a glucometer through modeling of circadian profiles, in accordance with one embodiment. The method 20 can be implemented in software, such as through the database 14 and program 15, and execution of the software can be performed on a computer system 10, such as described supra with reference to FIG. 1, as a series of process or method modules or steps. By way of overview, a patient's SMBG measurements and accompanying dosing of diabetes medications, including insulin and oral agents, are entered into a circadian profile that is stored in the structured database 14 on the glucometer 12. The circadian profile is implemented using a format that affords a one-to-one correspondence with the CG&MT mandated target ranges of blood glucose values and is organized as data records in the database 14. The circadian profile structures daily SMBG measurements and medication dosing into a data series of pre-meal and timed post-meal categories. A day is modeled as a complete data series, even though the actual patient data within a particular "day" may actually have been collected on different calendar days falling within the observational time frame. In one embodiment, each modeled day is divided into meal periods for breakfast, lunch and dinner, and one additional "meal" period from pre-bedtime through overnight to pre-breakfast, which is actually a period of fasting. Each data series includes one pre-meal SMBG value and diabetes medication dosing for each of breakfast, lunch, and dinner (three SMBG values) and one timed post-meal period SMBG value also for each of breakfast, lunch, and dinner (three more SMBG values), plus one timed post-meal period SMBG value both pre-bedtime and overnight. In addition, notations on daily lifestyle chronicling physical activity, diet and stress at each meal period, and daily body weight can be included in the data record. Still other patient- and treatment-related data can also be stored in the database 14 on the glucometer 12.

The program 15 implements a statistical engine that regards the blood glucose values as categories and not as a time series, that is, temporal events based on actual "clock" time. A time series creates a time vector problem. For example, consider the averaging of continuous diurnal glucose readings for a patient's breakfast. On one day, say, Saturday, breakfast may occur at 6:30 am, while the next day, the patient decides to sleep in and breakfast may consequently occur at 8:15 am. The later occurrence of Sunday's breakfast at 8:15 am causes that diurnal glucose reading to temporally coincide with the peak post-meal diurnal glucose reading of Saturday, which causes the averaging of the wrong blood glucose values. To avoid the time vector problem, the blood glucose data is transformed from a time series axis to a category axis, where the correct pre- and timed post-meal blood glucose values are collected according to their descriptive labels, not clock time. The use of categories enables the blood glucose value to be both predictable and modelable using a log-normal statistical distribution for a model day.

A further advantage of using a category axis is being able to automatically synchronize bolus and basal doses to both span the time period beginning at just before a meal period all the way through to just before the next meal period. Conventional insulin pump manufacturers often program basal rates according to clock times that may not necessarily correspond to pre-meal times. Diabetes patients 11 who use an insulin pump are typically given the freedom to change their meal times or even skip meals altogether. Consequently, a potentially hazardous situation could arise when a patient 11 delays or skips a meal that normally includes an increase or "jump" in basal rate. If the change in basal rate was triggered by the patient 11 indicating the real starting point of a meal, patient safety would be restored because the basal rate would not change until the actual start of the meal.

The formation of a circadian profile begins with collecting meal period data into the database 14 with the glucometer 12 (step 21), as further described infra with reference to FIG. 3. Meal period data collection includes both making SMBG measurements from a blood sample and identifying any diabetes medications dosed, including insulin and oral agents, for the patient 11 for meal periods occurring over a recent observational time frame, typically from the last seven days. The meal period data is then organized into a circadian profile (step 22), as further described infra with reference to FIG. 4. Meal period data is cumulatively collected from the patient 11 (step 23). Additional data is accepted from the patient 11 and preferably at least two typical measurements of pre-meal and post-meal SMBG are eventually collected for each meal period. Upon completion, the meal period data, including the completed circadian profile, is offloaded from the glucometer 12 onto the personal or laptop computer 15 or mobile computing device for processing by the program 14 (step 24).

The short-term, typically 7-day, time frame over recent glycemic management provided by the circadian profile has been shown to allow accurate prediction of blood glucose outcomes. As a result, a model of the expected values of near-term blood glucose values and their predicted errors can be created and visualized (step 25), as further described infra with reference to FIG. 5. The visualization identifies those meal periods that are accompanied by a predicted risk of hypoglycemia or occurrence of hyperglycemia, which the caregiver is urged to address with the patient 11 during consultation. In addition, the CG&MT target ranges or, if preferred, the caregiver's targets for the patient 11, can be superimposed over the visualized blood glucose prediction to enable the caregiver to evaluate likely excursions from well-managed glycemic care (step 26), as further described infra with reference to FIG. 6.

Through the visualized glycemic outcome model, incremental suggestions on possible changes to medication dosing can be provided, which the caregiver can interactively explore to evaluate likely near-term affect on the patient 11. The program 15 supports the interactive exploration and modeling of all manner of anti-diabetes drugs, including insulin, other injectable medications and oral agents. As selected by the caregiver, potential changes in medication dosing are visually propagated over the blood glucose prediction (step 27), as further described infra with reference to FIG. 8. Other steps to further the patient consultation are possible, such as reviewing weight control through body mass index calculation and body weight trend analysis.

Meal periods form a set of categories within which SMBG values and diabetes medication, including insulin and oral agents, are stored and statistically analyzed. FIG. 3 is a flow diagram showing a routine 30 for collecting meal period data into the circadian profile stored on the glucometer 12 for use in the method 20 of FIG. 2. First, the level of blood glucose is read by the glucometer 12 from a blood sample provided by the patient 11 on a disposable test strip 16 (step 31), then displayed to the patient 11 on the visual display 19. Each of the SMBG values is systematically validated (steps 32-38), as follows. To ensure accurate prediction of glycemic outcome, only recent and typical SMBG values are allowed. Recent (step 33) means that the SMBG value was obtained during the seven days preceding the next caregiver consultation. Other time frames are possible, but increasing the window beyond seven days undermines the value and meaningfulness of the SMBG data as reflective of current actual glycemic condition. In a further embodiment, accuracy is ensured by applying a date and time stamp to each SMBG value using a clock that is integral to the glucometer. However, the patient 11 can override the automated time and date stamp to label atypical SMBG values. Typical (step 34) means that each of the SMBG values is without qualifications or exception. For instance, an SMBG measurement taken following a substantial Thanksgiving Day feast would be atypical and would not be representative of the patient's typical diet.

When entering data, the patient 11 has the ability to flag SMBG values (step 39) as not being either recent (step 33) or typical (step 34) either by performing a point-and-click operation with his mouse or other pointing device, or by manually typing comments in an editable comments field in the circadian profile. The patient 11 also identifies the applicable meal period category, for instance, pre-breakfast, and the SMBG value is retained (step 35). The ability to flag atypical SMBG values enables a patient 11 to associate a particular SMBG value with one or more events that can help explain the departure from expected and typical SMBG levels, such as a high or low carbohydrate intake, exercise or physical activity, or stress, as further described below with reference to FIG. 11. These explanatory events can be graded in levels relative to their normal baseline. In a further embodiment, flagged atypical SMBG values can be differentially weighted for use in the determination of expected blood glucose values and predicted errors, as further described infra, discarded or used in any other way.

If the SMBG value is both recent and typical, which can be confirmed by the patient 11 using the input controls 18 on the glucometer 12, the patient 11 is prompted by the glucometer 12 through the visual display 19 to identify the applicable meal period category, for instance, pre-breakfast, and the SMBG value is retained (step 35). Data entry can be done all at once, or episodically, as convenient. As the program 15 can model insulin and most oral (tablet) or injected anti-diabetes drugs, the patient 11 also identifies using the input controls 18 any diabetes medications, including oral or injected anti-diabetic agents and insulin doses, which were taken or administered about the time that the blood glucose was measured by the glucometer 12 (step 36). Both basal and bolus insulin dosing, plus, optionally, the site of insulin injection on the patient's body, are identified. Insulin injection site provides a point of discussion between the caregiver and the patient 11 during consultation in light of the affect that injection site can have on insulin absorption and therefore the rate of glycemic regulation. The SMBG value and the diabetes medication dosing are stored directly into the database 14 by the glucometer 12 under the meal period category that was identified by the patient 11 (step 37). In a further embodiment, SMBG values and the diabetes medication dosing from a different glucometer can be entered, for instance, to accommodate situations where a patient has multiple glucometers for use at home, during work, while traveling, and so forth.

In one embodiment, only a single type of basal insulin, that is, longer-acting insulin with a physiologic mechanism of action principally spanning one half day to no more than one full day, and a single type of bolus insulin, that is, shorter-acting insulin with a physiologic mechanism of action principally spanning no more than three to eight hours, are accepted into the circadian profile. Other types of longer-acting and short-acting drugs in addition to or in lieu of insulin could also be accepted. However, dosing of different types of insulin having the same temporal mechanism of action, such as multiple simultaneous or overlapping short-acting insulin, is not permitted, as the net affect of arbitrarily combinable multiple insulin dosing is ambiguous and cannot be modeled with sufficient predictive certainty.

In a further embodiment, glucose lowering drugs, including shorter-, intermediate-, and longer-acting classes of anti-diabetes drugs, particularly oral hypoglycemia drugs, are modeled in addition to or in lieu of insulin. These medications include insulin sensitizers, including biguanides and thiazolidinediones; secretagogues, such as sulfonylureas and non-sulfonylurea secretagogues; alpha-glucosidase inhibitors; and peptide analogs, for instance, injectable incretin mimetics, injectable Glucagon-like peptide analogs and agonists, gastric inhibitory peptide analogs, dipeptidyl Peptidase-4 inhibitors, and injectable Amylin analogues. Other types of glucose lowering medications could also be accepted.

Finally, a minimum of two SMBG values per meal period are needed to form a complete circadian profile, one pre-meal measurement and one timed post-meal measurement, which, for statistical purposes, should be repeated a minimum of two times apiece for a total of 16 SMBG values, although more data, up to the maximum possible over a recent time frame, are possible. In one embodiment, a maximum of 56 SMBG values can be accepted, which account for one pre-meal SMBG value for breakfast, lunch, and dinner (three SMBG values) and one timed post-meal period SMBG value also for breakfast, lunch, and dinner (three more SMBG values), also a bedtime and an overnight (two SMBG values), over an entire seven-day week. The patient 11 continues to enter SMBG data (step 40) until all available data up to that time have been entered.

Conventional approaches to diabetes management are often retrospective in that changes in treatment are primarily based on historical, rather than recent, glycemic outcomes. In contrast, a circadian profile, as described herein, shifts the focus to recent indicators of glycemic condition and only for typical meal periods, which enables accurate prediction of short-term blood glucose and A1c outcomes. FIG. 4 is a user interface diagram showing, by way of example, an interactive screen 50 for a circadian profile 51 for use in the system 10 of FIG. 1. Although the glucometer 12 stores the patient's diabetes management data directly into a circadian profile in the database 14 for later offload to a personal or laptop computer 13 or mobile computing device, the interactive screen 50 can be generated by the program 15 for use by both the patient 11 and the caregiver during consultations to review, correct and fine tune the collected diabetes management data. In a further embodiment, the circadian profile can be uploaded back into the database 14, as further described infra.

The circadian profile fits within the "three-legged stool" metaphor of clinical diabetes management that focuses on body weight, A1c level and glycemic management. The creation of each circadian profile begins with assembling and organizing SMBG values and diabetes medication, as well as other relevant information that is stored into the database 14. The patient's and caregiver's demographics 52 are entered as an initial step. The remainder of the circadian profile 51 contains patient information that is organized under a series of pre-meal and timed post-meal categories 53. In one embodiment, eight categories 53 of meal periods are defined for breakfast, lunch and dinner: pre- and timed post-meal, pre-bedtime and overnight periods, although other category-based series are possible, including mid-meal periods. Within each category 53, the patient's body weight, SMBG values 54 and their times of measurement are entered, plus any diabetes medication 55 that was taken or administered. In addition, for those patients who are on injections of insulin, the site of injection is also entered, which provides a talking point during patient consultation. Finally, the patient 11 can enter optional comments 56 on lifestyle, including carbohydrate estimate ("CHO"), exercise or physical activity level ("EX"), stress, and so forth. The lifestyle comments are also points of possible discussion with the caregiver. Other patient data can also be collected, like blood pressure and resting heart rate.

Figure 5:
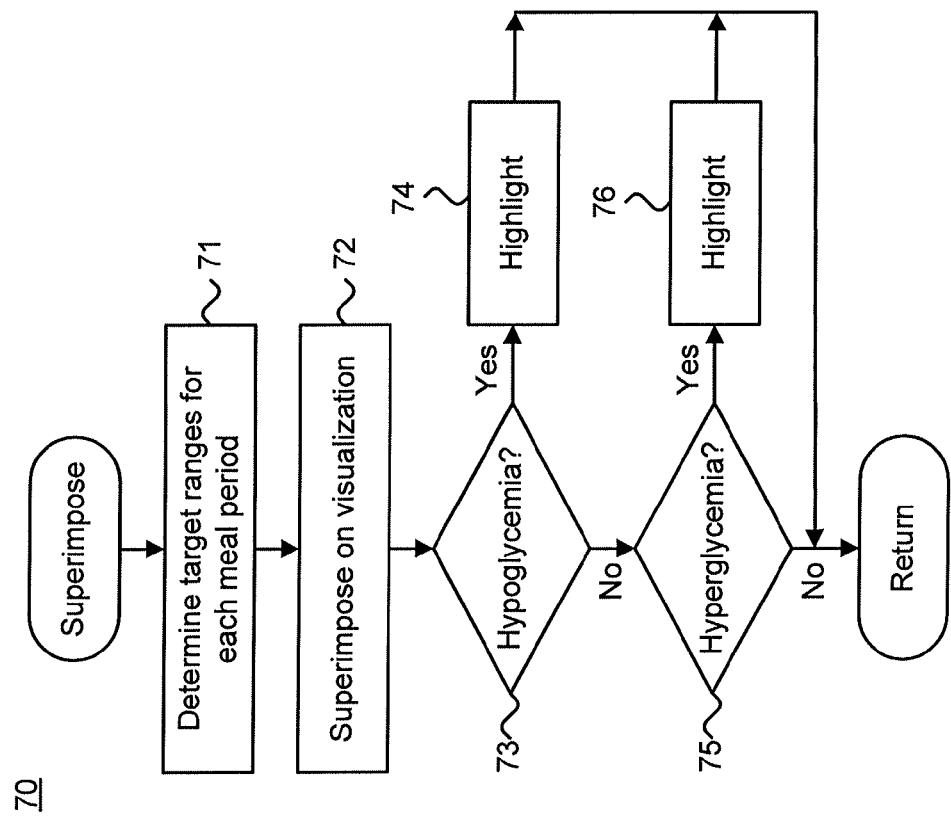
FIG. 5 is a flow diagram showing a routine for visualizing expected blood glucose values and predicted errors for use in the method of FIG. 2.

The categorization of recent typical SMBG values into a circadian profile enables accurate prediction and modeling of near-term blood glucose and A1c levels. FIG. 5 is a flow diagram showing a routine 60 for visualizing expected blood glucose values and predicted errors for use in the method 20 of FIG. 2. Each of the sets of meal period data is evaluated and modeled (steps 61-64), as follows. The expected blood glucose value and predicted error for each meal period on the category axis is first determined and a model of the expected blood glucose values and their respective predicted errors by meal periods is created for a model day (step 62). During the statistical determination of the expected blood glucose values and predicted errors, all SMBG values may be treated as having equal weight in terms of their respective influence on the prediction and modeling of near-term blood glucose and A1c levels. In a further embodiment, individual SMBG values can be flagged and differentially weighted based on a weighting criteria, such as used to flag atypical SMBG, as discussed supra, which causes the model to reflect the relative influence of each SMBG value based on its respective weight. Other ways of emphasizing or deemphasizing factors affecting SMBG monitoring are possible.

A seven-day window is used to generate the model. Recall that a replicated minimum of two SMBG values per meal period is preferred, although more data within the seven-day observational time frame are believed to improve accuracy. The statistical methods for performing the near-term blood glucose level prediction has been clinically validated for both efficacy and safety, such as described in A. M. Albisser et al., Home Blood Glucose Prediction: Validation, Safety, and Efficacy Testing in Clinical Diabetes, *Diabetes Tech. Ther.*, Vol. 7, pp. 487-496 (2006); and A. M Albisser et al., Home Blood Glucose Prediction: Clinical Feasibility and Validation in Islet Cell Transplantation Candidates, *Diabetologia*, Vol. 48, pp. 1273-1279 (2005), the disclosures of which are incorporated herein by reference.

Empirically and as scientifically demonstrated supra, when assembled into distinct pre- and timed post-meal categories, SMBG data follows a log-normal distribution. Consequently, the expected blood glucose value and predicted error for each meal period are visualized using a log-normal distribution (step 63), as further described infra with reference to FIG. 7. Statistically, each expected blood glucose value is the geometric mean of the SMBG values stored in the database 14 for the observational time frame and the predicted error is the standard deviation of the geometric mean. When the patient's blood glucose and A1C values are within target range, the type of statistical distribution used in the model becomes less crucial. As a result, in a further embodiment, a standard normal distribution can be used instead of a log-normal distribution. Under the same rationale, still other types of statistical distributions could also be used.

After all of the sets of meal period data have been evaluated and modeled, an A1c estimate is determined (step 65) for inclusion with the visualization. In one embodiment, the patient's A1c is derived from mean SMBG values, such as described in C. L. Rohifing et al., Defining the Relationship Between Plasma Glucose and HbA(1c): Analysis of Glucose Profiles and HbA(1c) in the Diabetes Control and Complications Trial, *Diabetes Care*, Vol. 25(2), pp. 275-8 (2002), the disclosure of which is incorporated by reference.

With a circadian profile 51 for a diabetic patient 11, a caregiver is able to apply a "treat to target" approach, as presented through a visual display of glucose management data, that focuses on moving the patient's SMBG values into target ranges that represent recognized well-managed glycemic control, as opposed to merely keeping A1e below a certain point. FIG. 6 is a flow diagram showing a routine 70 for superimposing target ranges over the expected blood glucose values and predicted errors for use in the method 20 of FIG. 2. The one-to-one correspondence between the meal periods in each circadian profile 51 and the CG&MT mandated target ranges enables the expected blood glucose levels and the target ranges to be visualized together.

As an initial step in the approach, the target blood glucose level ranges for each meal period are determined for the diabetes patient 11 (step 71). The target ranges are then visually superimposed over the expected blood glucose levels and the ranges (step 72). The target ranges can either be from the CG&MT or as specified by the caregiver. In one embodiment, different sets of target ranges can be used, including a "default" target range, a gestational diabetes target range (women only) and a target range for use in breaking insulin resistance. The default target range specifies a pre-meal target of 80 mg/dL<SMBG value<140 mg/dL and a post-meal target of 80 mg/dL<SMBG value<180 mg/dL, regardless of whether the meal period is breakfast, lunch or dinner. The gestational target range decreases the pre-meal target range to 60 mg/dL<SMBG value<120 mg/dL. The insulin resistance target range raises the pre-meal target to 120 mg/dL<SMBG value<180 mg/dL, which has the affect of providing the patient 11 with a reason to reduce medication dosing by moving his SMBG values into the (raised) target range, instead of continually increasing medication in a futile attempt to reach the mandated target range. Once the insulin-resistant diabetes patient 11 has achieved the raised insulin resistance breaking target, the default target range can again be approached in steps.

The treat-to-target approach is equally applicable to controlling hyperglycemic occurrence and hypoglycemic risk, where medication must respectively be increased or decreased. The expected blood glucose level in each meal period is respectively compared to hypoglycemic and hyperglycemic thresholds (steps 73 and 75) and, if a risk exists, the meal period is highlighted and a notice is displayed to inform the patient 11 and his caregiver (steps 74 and 76). In one embodiment, a hypoglycemic threshold of 50 mg/dL and a post-meal hyperglycemic threshold of 180 mg/dL are used, where an expected blood glucose level falling outside of either threshold will trigger an appropriate warning. The treat-to-target approach also dovetails well with dietary educational efforts in which the patient 11 is taught to either decrease or increase carbohydrate intake to respectively avoid onset of hyperglycemia or hypoglycemia.

Figure 7:
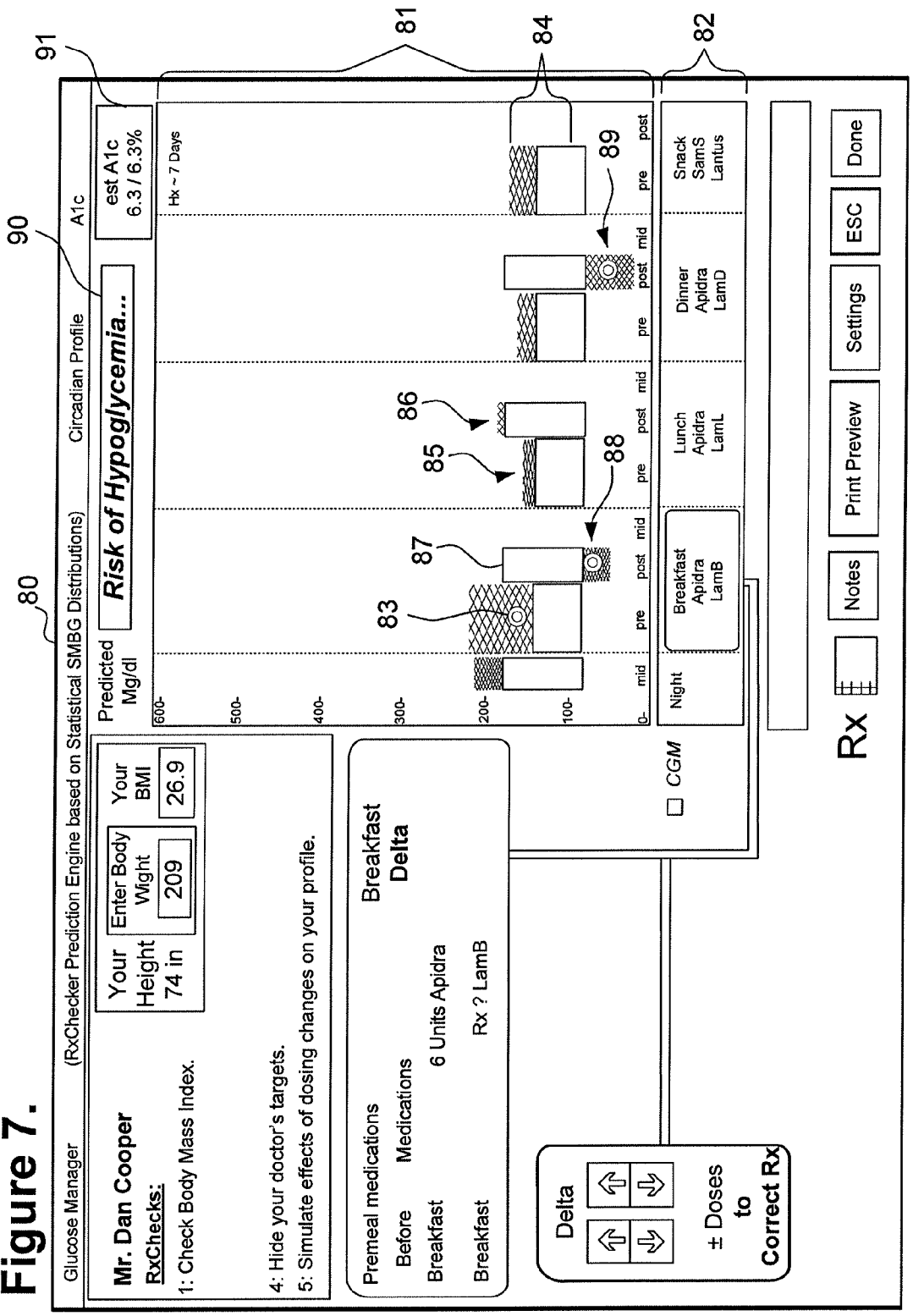
FIG. 7 is a user interface diagram showing, by way of example, an interactive screen for visualizing and evaluating the expected blood glucose values and predicted errors for use in the system of FIG. 1.

The treat-to-target approach is facilitated through a graphical visualization of the model of the expected blood glucose values and predicted errors with mandated target ranges superimposed. FIG. 7 is a user interface diagram showing, by way of example, an interactive screen 80 for visualizing and evaluating the expected blood glucose values and predicted errors for use in the system 10 of FIG. 1. Since the program 15 does not make changes to the patient's course of treatment per se and only provides guidance, the screen 80 can be used by both the patient and the caregiver, as well as other users.

The visualization groups the expected blood glucose values and their respective predicted errors in the model 81 by meal periods 82 for a model day. The model 81 represents the patient's expected blood glucose values 83 and predicted errors 84 before predicted affects of medication dosing increments. Each of the meal periods 82 includes categories 85, 86 for a pre-meal and a timed post-meal expected blood glucose value 83 and a predicted error 84. Due to the log-normal distribution, the predicted error 84 above and below an expected blood glucose value 83 is not symmetric and a wider predicted error 84 appears above each expected blood glucose value 83 than below. The target ranges 87 are superimposed over each of the expected blood glucose values 83. When the probability risk is greater than 5%, or other selectable range, that the expected blood glucose values 88, 89 will fall below the hypoglycemic threshold, the risk is flagged with a warning 90 displayed to the user. As a result, those meal periods where predicted blood glucose values may fall out of target range can be readily identified by the caregiver and patient alike. Finally, the estimated A1c 91 derived from mean SMBG values is displayed.

Figure 8:
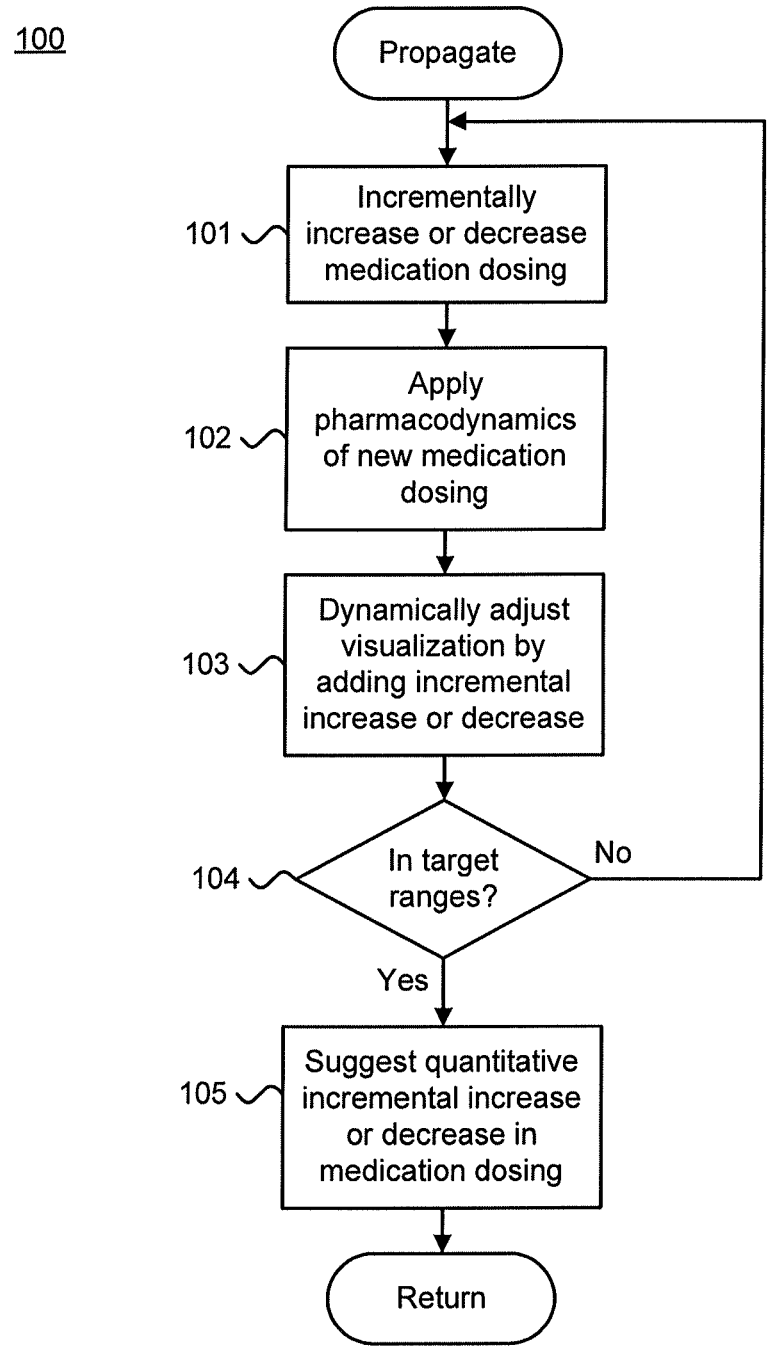
FIG. 8 is a flow diagram showing a routine for propagating an incremental change in medication dosing for use in the method of FIG. 2.

The visualization of the expected blood glucose values and predicted errors, and target ranges provides a starting point for the caregiver to begin working with the patient 11. Changes to diabetes medication, particularly medication dosing, may be necessary to move the SMBG values into target range. FIG. 8 is a flow diagram showing a routine 100 for propagating an incremental change in medication dosing for use in the method 20 of FIG. 2. The expected glucose values, as modified by the pharmacodynamics of any medication dosing changes contemplated for the patient 11, enable the program 15 to suggest quantitative changes to medication dosing for caregiver or patient 11 consideration. The program 15 can also generate qualitative feedback. Generating quantitative feedback provides a closed-loop treatment model. For safety, allowable incremental changes in medication dosing are limited in amount to achieve the targets more slowly, but safely, and without the risk of limit cycling. However, to accommodate the slower physiological response of these smaller incremental changes, the patient 11 has to measure SMBG more often, up to six times per day, than with a qualitative approach that works with fewer SMBG values.

The amount of change in medication dosing, based on the diabetes medications already identified by the patient 11, can be determined by either incrementally increasing or decreasing the amount of the dosed medication in the model 81 (step 101). The pharmacodynamics of the diabetes medication is applied in proportion to the incremental change in dosing, as incrementally increased or decreased (step 102), and the visualization is dynamically adjusted by adding the incremental increase or decrease in blood glucose level to the expected blood glucose values 83 (step 103). The program 15 uses the pharmacodynamics of the diabetes medications to model the affect on the expected values of near-term blood glucose values and their predicted errors. Drug manufacturers formulate their drugs, so that an incremental change in dosing, amounting to the smallest dosing unit, such as a half tablet of an oral medication of the lowest strength or one IU of an injectable medication, produces a glucose lowering effect similar to all the other anti-diabetes drugs in its class. This "normalization" is used to avoid having their drug require different dosing profiles when compared to comparable drugs offered by their competitors, where, for instance, one manufacturer's medication may require three oral tablets while a competitor's medication only requires a single oral tablet.

The normalization of comparable anti-diabetes medications is reflected in the visualization, which allows a user to change medication dosing incrementally (steps 101-103) until the expected blood glucose values move into the target ranges (step 104). The pharmacodynamics allow one "click" on the user interface to reflect a similar glucose lowering affect for all anti-diabetes drugs in the same class, although the pharmacodynamics of different drug classes are applied in such a way as to normalize the area under the response curves to reflect the total drug administered. As a result, longer-acting drugs have a lower peak, but last longer to keep the area under the blood glucose curve similar to the same amount of a shorter-acting drug, which has a higher peak and short duration of action.

That amount of incremental increase or decrease in the dosed medication is then presented to the caregiver as an incremental suggested change in medication dosing (step 105). The qualitative scale is slight, moderate, or significant, although in a further embodiment, this scale can also be expressed quantitatively. Specifically, the program 15 scales six left whole-clicks or twelve right half-clicks to span the range from slight qualifiers (+), to moderate qualifiers (++), and finally to significant qualifiers (+++) for all dosage increments, or decrements, which allows "clicks" to be quantified into usable measures of dosing, such as half oral tables or IUs of insulin. In addition, the program 15 provides a mechanism for simply "accepting" or documenting medication changes, such that those changes that are pre-populated when the patient 11 enters SMBG readings and verifies the doses taken.

In a further embodiment, the circadian profile and incremental increase or decrease in the dosed medication could be uploaded back onto the glucometer 12, depending upon whether the glucometer 12 is used as a dosing treatment controller, where the incremental changes are uploaded, or a regimen guidance tool, in which the incremental changes are maintained separately and offline from the glucometer 12.

The decision on how to use the glucometer 12 in diabetes management and uploading the incremental changes into the onboard database turns on whether such usage is thought of as being inside or outside the treatment arc that connects the output of the glucometer 12 to the "tip of the needle," that is, the drug delivery device. The incremental changes would be uploaded back on to the glucometer 12 if the onboard database is intended to be portable and the patient 11 intends to run the program 15 on any personal or laptop computer 13 or mobile computing device without the benefit of a virtualized database provided through a "cloud" computing infrastructure. However, incremental change uploading can potentially become cumbersome if the patient 11 has more than one glucometer 12 actively in use, such as at home and at work, and keeping the databases on each of those devices current could become a logistical challenge to the patient 11 and his caregiver.

Figure 9:
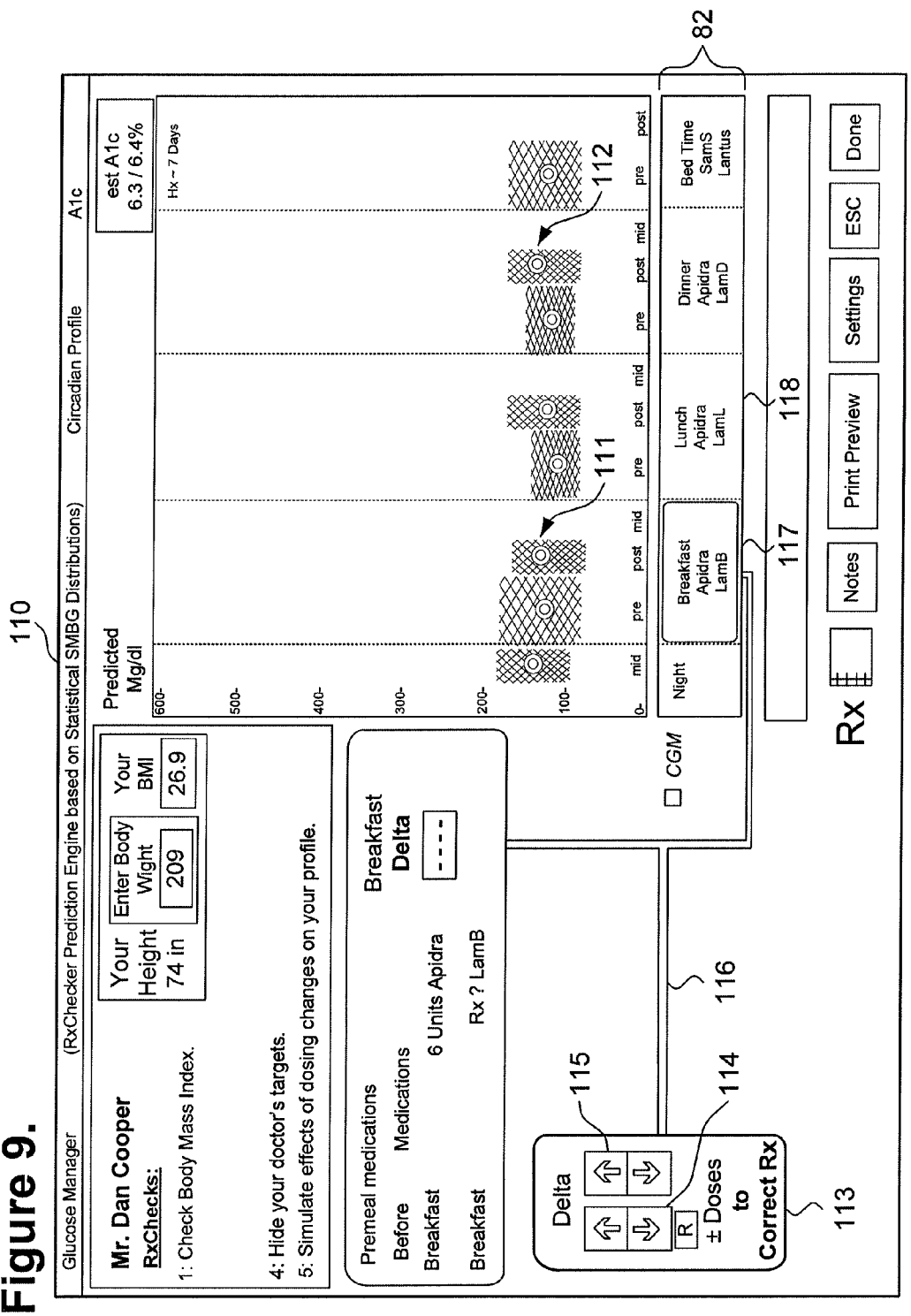
FIGS. 9 and 10 are user interface diagrams showing, by way of example, interactive screens for modeling incremental changes in medication dosing for use in the system of FIG. 1 respectively before and after superimposing the target ranges.
Figure 10:
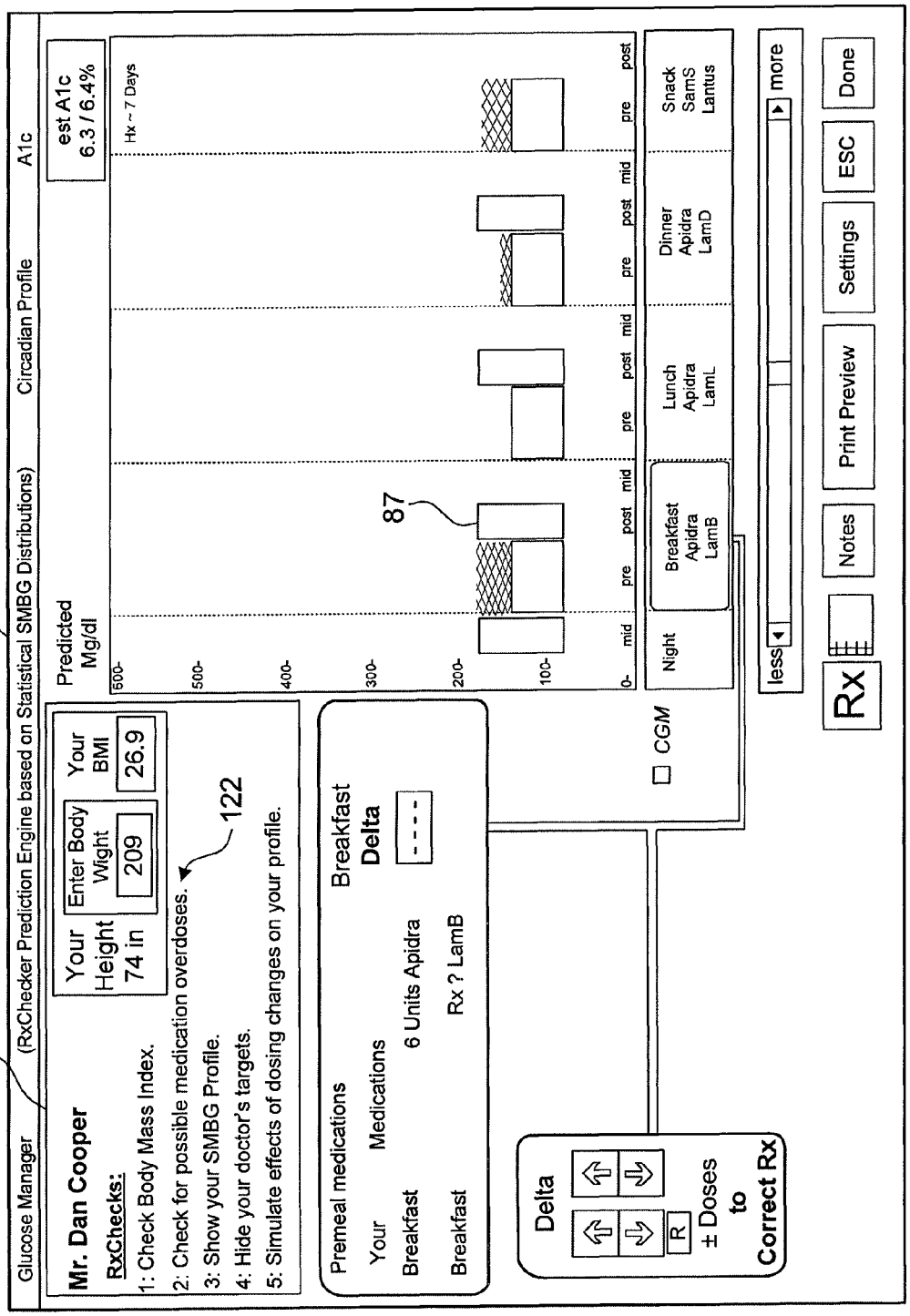

Throughout exploration of potential medication dosing changes, including insulin and oral agents, the possible affect of any suggested change, or other amount of change in medication dosing desired, is added to the visualization by dynamically adjusting the expected glucose values based on the relative pharmacodynamics of the new medication dosing change. FIGS. 9 and 10 are user interface diagrams showing, by way of example, interactive screens 110, 120 for modeling incremental changes in medication dosing for use in the system 10 of FIG. 1 respectively before and after superimposing the target ranges. Referring first to FIG. 9, with the new medication dosing, the two expected blood glucose values 111, 112 that formerly risked hypoglycemia at a 5%, or greater probability are now safely raised and the risk of hypoglycemia has been removed. In addition to the actual medications described (Apidra and Lantus), the fields in the descriptor bar for meal periods 82 include placeholders at the breakfast, lunch and dinner meal periods for longer-acting (insulin) medications ("LamB," "LamL" "LamD") and at only the bedtime "meal" period for shorter-acting (insulin) medication ("SamS").

In a still further embodiment, a caregiver can model proposed changes to medication dosing and, through the cloud storage infrastructure, feed the results back to the patient's personal or laptop computer 13, mobile computing device, portable media device 12, glucometer 17 or other type of portable blood glucose testing device with onboard data collection capabilities, as applicable. In addition, manufacturers of glucose meters and glucose sensing strips that are able to monitor their devices can also be participants to the caregiving process. These manufacturers can provide continued calibration and other performance metrics that will assure quality, accuracy, and safety in their measuring devices and signal an unsafe or unreliable status, which would flag a reading as possibly atypical or unreliable.

Changes to the dosed medications, whether insulin or oral agents, can be explored by the user through a control panel 113 (labeled "±Doses to Correct Rx"). Within the control panel 113, controls 114, 115 under the label "Delta" respectively allow the user to explore incrementally increasing or decreasing the shorter-acting and longer-acting medications for a meal period 82, as indicated by a connector line 116. The sub-control button (labeled 'R.') serves as a shortcut to reset any explored increments back to zero. Here, the breakfast meal period 117 is selected with the shorter-acting medication set to Apidra and the longer-acting medication set to LamB, which is, an as-yet unspecified, longer acting medication at B. To explore the impact of medication dosing changes during other meal periods 82, for instance, the lunch meal period 118, the user selects the area labeled "Lunch,"

upon which the lunch meal period 118 is connected by the connector line 116 to the control panel 113 and the breakfast meal period 117 is deselected.

In one embodiment, the change in insulin dosing can be presented in standard dosage IUs (International Units), in increments of tenths of an IU, where the scaling is rationalized for the patient's delivery device. For instance, hypodermic syringes have a scale that depends on their full volume, whereas insulin injection pens dose in increments of 1 IU or 2 IU per click. Insulin pumps are capable of doing in increments of 0.1 IU. However, in practice, insulin dosing can be course when the dose is over 10 IU and finer for infants whose dose could be ~1 IU, such as 1.5 IU or 0.5 IU. In suggesting the final change in insulin dosing to the patient 11 or caregiver, the quantitative dose suggestion could follow a conversion of clicks for an insulin injection pen or some other individualized scaling factor that depends on the size of the total daily dose. Quantifying the clicks to tablets conversion could be by 0.5 tablets up to a maximum of 1 to 3 tablets, or limited by the maximum meal and daily allowable amounts.

The expected blood glucose value 83 and predicted error 84 for each meal period 82 are adjusted for the pharmacodynamics of the changes to the diabetes medication being explored. Typically, the pharmacodynamics follow the dose-response characteristic. The pharmacodynamics define the effect of the drugs, that is, the patient's diabetes medication, on blood glucose. The pharmacodynamics of each type of drug is available from the manufacturer. Beginning with the meal period at which the diabetes medication change was administered, the pharmacodynamics are used to raise or lower the expected level of blood glucose in the visualization until the propagated pharmacodynamics are fully exhausted. Depending upon the particular drug's pharmacodynamics, the expected blood glucose levels in a sequence of several adjacent meal periods may be affected. For instance, insulin glargine taken as a basal dose is long-acting and the pharmacodynamics will affect meal periods for several days, although the insulin's ability to lower blood glucose level after the first 24 hours is significantly diminished. As well, insulin taken as a pre-meal bolus dose is short-acting, yet the pharmacodynamics may well equally propagate for an entire day, albeit of relatively small continuing blood glucose level-lowering affect. However, the cumulative pharmacodynamics of all of the basal doses and each of the bolus doses taken throughout the observational time frame may nevertheless lower the expected blood glucose level at any given meal period more than a single bolus dose would if taken at that same meal period in isolation from any other insulin doses.

Following (or during) the exploration of changes to the medication dosing, including insulin or oral agents, the target ranges 87 can be superimposed to provide visual guidance as to whether the new medication dosing will satisfactorily move the expected blood glucose values 83 into the mandated targets and avoid both the risk of hypoglycemia and occurrence of hyperglycemia. Referring next to FIG. 10, the target ranges 87 have been superimposed above the expected blood glucose values 83 and predicted errors 84. All of the patient's expected blood glucose values 83 are within target and reflect ideal glycemic control. In addition, the caregiver is able to also ensure proper dosing of medications through a set of prescription checkers steps ("RxChecks") 121 that includes a control 122 to "Check for possible medication overdoses," which checks that medication is dosed within safe limits at each meal period and for the entire day. Other types of prescription checks and safeguards are possible.

Atypical SMBG values can also serve to guide the medication dosing adjustment processes. FIG. 11 is a user interface diagram showing, by way of example, an interactive screen 130 for a circadian profile for use in a further embodiment of the system 10 of FIG. 1. The SMBG values 131 and their times of measurement are entered along with an explanation 132 that flags an atypical SMBG value for the lunch meal period. Other labels within the various interactive screens, such as the label accompanying RxChecks steps 121 (shown in FIG. 10), can be highlighted to call attention to unusual events that may lead to atypical SMBG data. Atypical or "unusual" events touch on aspects of the patient's diet, exercise, physical activity, stress, and similar often unavoidable outcomes of activities of daily living, for example, eating an atypical amount of carbohydrates (either more or less than normal, as happens on Thanksgiving Day) without a matching correction bolus, experiencing more or less stress than usual, or engaging in an unusual amount of exercise or physical activity.

In one embodiment, a flagged event triggers the display of a notice to a tooltip associated with the associated post- and mid-meal glucose ranges, that is, "After L" and "Mid L-D." Here, the notice would say, for instance, "Unusual CHO or unusual activity in this MP may distort this prediction." Similarly, for the following pre-meal glucose range in the following meal period, that is, "Pre D," the notice would say, for instance, "Preceding unusual ±CHO or unusual activity may distort this prediction." Also, as a further guide in deciding whether to accept or ignore a potentially atypical expected blood glucose value and its range, a tooltip can also be associated with the low end of the predicted range 88 (shown in FIG. 7) for a meal period category, such as "Before L," that includes the acceptable SMBG reading in the range for that meal category. This tooltip notice can be helpful in understanding why a warning about a factitious risk of hypoglycemia that arises from an outlying hyperglycemia event can safely be ignored. Other types and triggers of notice are possible.

While the invention has been particularly shown and described as referenced to the embodiments thereof, those skilled in the art will understand that the foregoing and other changes in form and detail may be made therein without departing from the spirit and scope of the invention.

What is claimed is:

1. A computer-implemented method for improving glucose management with a glucose meter through modeling of circadian profiles, comprising the steps of:

defining a plurality of meal periods that each occur each day at a set time;

building a circadian profile for a diabetic patient, comprising the steps of:

choosing an observational time frame for the circadian profile comprising a plurality of days that have occurred recently;

collecting at least two sets of pre- and post-meal period data that were recorded at each of the meal periods that occurred each day in the observational time frame and stored on a glucose meter;

reading a level of blood glucose on a test strip provided to the glucose meter by the diabetic patient for each of the meal periods;

identifying doses of diabetes medication, which were respectively taken during each of the meal periods as the readings of the blood glucose levels; and storing the blood glucose level and the diabetes medication doses into the circadian profile in a record for each of the meal periods; and creating a model of glucose management for the diabetic patient, comprising the steps of:

defining a modeling period comprising a plurality of days, which each comprise the same plurality of the meal periods that occurred each day in the observational time frame;

estimating expected blood glucose values and their predicted errors at each of the meal periods occurring each day in the modeling period from the blood glucose levels in each record based on the meal periods in the circadian profile that respectively occur at the same set times and visualizing the expected blood glucose values and their predicted errors over time for each meal period occurring each day in the modeling period in a log-normal distribution;

determining target ranges for blood glucose at each of the meal periods occurring each day in the modeling period and superimposing the target ranges over the expected blood glucose values for each meal period occurring each day in the modeling period in the log-normal distribution;

selecting one of the meal periods that occurs on one of the days in the modeling period and modeling a change in the dose of the diabetes medication for the selected meal period, comprising the steps of:

obtaining a dose-response characteristic comprising a blood glucose lowering effect over time for the modeled change in the dose of the diabetes medication, wherein the blood glucose lowering effect has been normalized with blood glucose lowering effects of diabetes medications based on the same change in the dose;

propagating the normalized blood glucose lowering effect over time for the modeled change in the dose of the diabetes medication to the expected blood glucose values, beginning with the selected meal period and continuing with each of the meal periods occurring subsequently in the modeling period, the normalized blood glucose lowering effect being adjusted in proportion to the set time of each subsequent meal period until the normalized blood glucose lowering effect is exhausted; and visualizing the expected blood glucose values as propagated and their predicted errors in the log-normal distribution, wherein the steps of building the circadian profile are performed on a suitably-programmed glucose meter and the steps of creating the model are performed on a suitably-programmed computer.

2. A method according to claim 1, further comprising the steps of:
modeling an incremental change in the dose of the diabetes medication for the selected meal period;
applying the normalized blood glucose lowering effect of the diabetes medication in proportion to the dose as incrementally changed until the expected blood glucose values in the log-normal distribution move into the target ranges; and
providing the incrementally changed dose of the diabetes medication as a suggested incremental dosing change.

3. A method according to claim 1, further comprising the steps of:
defining a threshold of hypoglycemic risk expressed as a blood glucose value; and
identifying each of the expected blood glucose values in the log-normal distribution exhibiting a risk of falling below the hypoglycemic risk threshold.

4. A method according to claim 1, further comprising the steps of:
defining a threshold of hyperglycemic occurrence expressed as a blood glucose value; and
identifying each of the expected blood glucose values in the log-normal distribution exhibiting a risk of rising above the hyperglycemic occurrence threshold.

5. A method according to claim 1, further comprising the step of:
defining the meal periods as comprising, within each day, breakfast, lunch, dinner, and bedtime meal periods.

6. A method according to claim 1, further comprising the step of:
deriving the target ranges for the blood glucose from high and low blood glucose values as published in consensus practice guidelines or as specified by a caregiver of the diabetic patient.

7. A method according to claim 1, further comprising the step of:
modeling the diabetes medication as no more than one shorter-acting drug, which comprises a physiologic mechanism of action principally spanning no more than three to eight hours, and one longer-acting drug, which comprises a physiologic mechanism of action principally spanning one half day to no more than one full day.

8. A method according to claim 1, further comprising the step of:
modeling the diabetes medication as a glucose lowering medication taken by the diabetic patient either in addition to or in lieu of insulin.

9. A method according to claim 1, further comprising the step of:
deriving expected glycated hemoglobin from a mean of readings of the blood glucose levels during the observational time frame.

10. A method according to claim 1, further comprising the step of:
collectively adjusting the target ranges for the blood glucose at each of the meal periods occurring each day in the modeling period upward or downward based on a physiological condition specific to the diabetic patient.

11. A method according to claim 1, further comprising the steps of:
including a body weight of the diabetic patient in the circadian profile; and
performing a trend analysis of the body weight over any preceding observational time frames.

12. A non-transitory computer readable storage medium storing code for executing on a computer system to perform the method according to claim 1.

13. A blood glucose meter for managing diabetes with circadian profiles, comprising:
an electronically-stored database implemented on a glucose meter and comprising a plurality of records, each record comprising a circadian profile, comprising:
a plurality of meal period categories that each occur each day at a set time and divide each circadian profile into the meal period categories;
an observational time frame comprising a plurality of days that have occurred recently;
at least two of typical measurements of pre-meal and post-meal self-measured blood glucose that were recorded at each of the meal period categories that occurred each day in the observational time frame; and
doses of diabetes medication that were respectively taken during each of the meal period categories for which the blood glucose measurements were recorded; and an executable application stored on the glucose meter and configured to execute on a suitably-programmed computer to model glucose management, comprising:
    a collection module configured to offload the database from the glucose meter and to collect the blood glucose measurements along a category axis comprising each of the meal period categories;
    a statistical engine configured to determine expected blood glucose values and their predicted errors at each of the meal period categories occurring each day in the modeling period from the blood glucose measurements based on the meal period categories on the category axes in the circadian profile that respectively occur at the same set times and to visualize the expected blood glucose values and their predicted errors over time for each meal period category occurring each day in the modeling period in a log-normal distribution on the computer; and
    a change modeling module configured to select one of the meal period categories that occurs on one of the days in the modeling period and to model a change in the dose of the diabetes medication for the selected meal period category, comprising:
        a dose-response characteristic module configured to obtain a dose-response characteristic comprising a blood glucose lowering effect over time for the modeled change in the dose of the diabetes medication, wherein the blood glucose lowering effect has been normalized with blood glucose lowering effects of diabetes medications based on the same change in the dose;
        a dosing module configured to propagate the normalized blood glucose lowering effect for the modeled change in the dose of the diabetes medication to the expected blood glucose values, beginning with the selected meal period category and continuing with each of the meal period categories occurring subsequently in the modeling period, the normalized blood glucose lowering effect being adjusted in proportion to the set time of each subsequent meal period category until the normalized blood glucose lowering effect is exhausted; and
        a visualization module configured to visualize the expected blood glucose values as propagated and their predicted errors in the log-normal distribution.

14. A glucose meter according to claim 13, further comprising:
    target ranges stored in the database for the expected blood glucose values at each of the meal period categories occurring each day in the modeling period in the log-normal distribution; and
    a target module configured to superimpose the target ranges over the expected blood glucose values for each meal period category occurring each day in the modeling period in the log-normal distribution on the computer.

15. A glucose meter according to claim 14, further comprising:
    an incremental dosing submodule configured on the computer to model an incremental and quantitative change in the dosing dose of the diabetes medication for the selected meal period category, to adjust the expected blood glucose values and their predicted errors in the log-normal distribution based on the normalized blood glucose lowering effect of the diabetes medication in proportion to the dose as incrementally quantitatively changed until the expected blood glucose values in the log-normal distribution move into the target ranges, and to suggest the incrementally quantitatively changed dose of the diabetes medication.

16. A glucose meter according to claim 13, further comprising:
    a threshold of at least one of hypoglycemic risk and hyperglycemic occurrence, which are both expressed as blood glucose values stored in the database; and
    a warning module configured on the computer to identify each of the expected blood glucose values in the log-normal distribution exhibiting either a risk of falling below the hypoglycemic risk threshold or rising above the hyperglycemic occurrence threshold.

17. A computer-implemented method for managing diabetes using a glucose meter with circadian profiles, comprising the steps of:
    structuring a database on a glucose meter comprising a plurality of records, each record comprising a circadian profile, comprising:
        defining a plurality of meal period categories that each occur each day at a set time and dividing each circadian profile into the meal period categories;
        choosing an observational time frame for the circadian profile comprising a plurality of days that have occurred recently;
        storing at least two of typical measurements of pre-meal and post-meal self-measured blood glucose that were recorded at each of the meal period categories that occurred each day in the observational time frame; and
        identifying doses of diabetes medication that were respectively taken during each of the meal period categories for which the blood glucose measurements were recorded; and
    storing a program on the glucose meter for modeling glucose management on a suitably-programmed computer, comprising:
        defining a modeling period comprising a plurality of days, which each comprise the same plurality of the meal period categories that occurred each day in the observational time frame;
        collecting the blood glucose measurements along a category axis comprising each of the meal period categories;
        determining expected blood glucose values and their predicted errors at each of the meal period categories occurring each day in the modeling period from the blood glucose measurements based on the meal period categories on the category axes in the circadian profile that respectively occur at the same set times and visualizing the expected blood glucose values and their predicted errors over time for each meal period category occurring each day in the modeling period in a log-normal distribution; and
        selecting one of the meal period categories that occurs on one of the days in the modeling period and modeling a change in the dose of the diabetes medication for the selected meal period category, comprising:
            obtaining a dose-response characteristic comprising a blood glucose lowering effect over time for the modeled change in the dose of the diabetes medication, wherein the blood glucose lowering effect has been normalized with blood glucose lowering effects of diabetes medications based on the same change in the dose;

propagating the normalized blood glucose lowering effect for the modeled change in the dose of the diabetes medication to the expected blood glucose values, beginning with the selected meal period category and continuing with each of the meal period categories occurring subsequently in the modeling period, the normalized blood glucose lowering effect being adjusted in proportion to the set time of each subsequent meal period category until the normalized blood glucose lowering effect is exhausted; and visualizing the expected blood glucose values as propagated and their predicted errors in the log-normal distribution, wherein the modeling steps are performed on the computer.

18. A method according to claim 17, further comprising the steps of:

determining target ranges for the expected blood glucose values at each of the meal period categories occurring each day in the modeling period; and superimposing the target ranges over the expected blood glucose values for each meal period category occurring each day in the modeling period in the log-normal distribution on the computer.

19. A method according to claim 18, further comprising the steps of:

modeling an incremental and quantitative change in the dose of the diabetes medication for the selected meal period category on the computer;

adjusting the expected blood glucose values and their predicted errors in the log-normal distribution based on the normalized blood glucose lowering effect of the diabetes medication in proportion to the dose as incrementally quantitatively changed until the expected blood glucose values in the log-normal distribution move into the target ranges; and suggesting the incrementally quantitatively changed dose of the diabetes medication.

20. A method according to claim 17, further comprising the steps of:

defining a threshold of at least one of hypoglycemic risk and hyperglycemic occurrence, which are both expressed as blood glucose values; and identifying on the computer each of the expected blood glucose values in the log-normal distribution exhibiting either a risk of falling below the hypoglycemic risk threshold or rising above the hyperglycemic occurrence threshold.

21. A non-transitory computer readable storage medium storing code for executing on a computer system to perform the method according to claim 17.

* * * * *